(12) United States Patent
Joos et al.

(10) Patent No.: US 8,655,431 B2
(45) Date of Patent: Feb. 18, 2014

(54) APPARATUS AND METHOD FOR REAL-TIME IMAGING AND MONITORING OF AN ELECTROSURGICAL PROCEDURE

(75) Inventors: Karen Joos, Nashville, TN (US); Jin Hui Shen, Nashville, TN (US); M. Shane Hutson, Nashville, TN (US); John Kozub, Mount Juliet, TN (US)

(73) Assignee: Vanderbilt University, Nashville, TN (US)

( * ) Notice: Subject to any disclaimer, the term of this patent is extended or adjusted under 35 U.S.C. 154(b) by 71 days.

(21) Appl. No.: 13/149,502

(22) Filed: May 31, 2011

(65) Prior Publication Data

US 2012/0310042 A1 Dec. 6, 2012

(51) Int. Cl.
*A61B 5/06* (2006.01)
*A61B 1/07* (2006.01)
*A61B 18/20* (2006.01)

(52) U.S. Cl.
USPC .............................. 600/427; 600/108; 606/13

(58) Field of Classification Search
USPC ......... 600/101, 108, 129, 160, 427, 473, 476, 600/478; 606/4, 10, 13, 27, 32, 46
See application file for complete search history.

(56) References Cited

U.S. PATENT DOCUMENTS

| | | | |
|---|---|---|---|
| 4,298,785 A | 11/1981 | Krenzer et al. | |
| 4,705,886 A | 11/1987 | Levenson et al. | |
| 5,921,926 A | 7/1999 | Rolland et al. | |
| 5,951,543 A * | 9/1999 | Brauer | 606/10 |
| 6,047,218 A | 4/2000 | Whayne et al. | |
| 6,072,765 A | 6/2000 | Rolland et al. | |
| 6,141,577 A | 10/2000 | Rolland et al. | |

(Continued)

FOREIGN PATENT DOCUMENTS

| | | |
|---|---|---|
| JP | 2004045322 | 2/2004 |
| WO | 2004023992 | 3/2004 |

(Continued)

OTHER PUBLICATIONS

OCT Intravascular Imaging System and OCT ImageWire; Goodman Co., Ltd. (Nagoya, Japan); OCT products developed by Goodman's U.S. subsidiary, LightLab Imaging; http://www.goodmankk.com; http://www.lightlabimaging.com/intl/company/about.htm; information available prior to May 31, 2011.

(Continued)

*Primary Examiner* — Michael Rozanski
(74) *Attorney, Agent, or Firm* — Michael Best & Friedrich LLP

(57) ABSTRACT

An optical coherence tomography probe and laser combination device configured for real-time z-directional guidance of the incisional depth of a surgical procedure. It can be used alone or placed within the working channel of an endoscope. The device includes an OCT single mode fiber, and a laser fiber or laser hollow waveguide or electrical surgical wire positioned adjacent to the OCT single mode fiber. The single mode fiber is configured to move laterally when activated by an actuator to scan light data reflected from a sample that is positioned in front of a distal end of the device. The light data can be processed to generate a B-scan image. The device can collect data in real-time during lasing, or immediately prior to and following the cutting. The surgical tool, when coupled to a processor, can deactivate when the B-scan image identifies that the incision is within a predefined tolerance.

28 Claims, 25 Drawing Sheets

(56) References Cited

U.S. PATENT DOCUMENTS

| | | | |
|---|---|---|---|
| 6,485,413 B1 * | 11/2002 | Boppart et al. | 600/160 |
| 6,507,747 B1 | 1/2003 | Gowda et al. | |
| 6,522,407 B2 | 2/2003 | Everett et al. | |
| 6,527,708 B1 | 3/2003 | Nakamura et al. | |
| 6,564,087 B1 | 5/2003 | Pitris et al. | |
| 6,564,089 B2 | 5/2003 | Izatt et al. | |
| 6,608,684 B1 | 8/2003 | Gelikonov et al. | |
| 6,615,072 B1 | 9/2003 | Izatt et al. | |
| 6,636,755 B2 | 10/2003 | Toida | |
| 6,668,185 B2 | 12/2003 | Toida | |
| 6,903,854 B2 | 6/2005 | Gelikonov et al. | |
| 6,975,898 B2 | 12/2005 | Seibel | |
| 6,999,608 B2 | 2/2006 | Toida | |
| 7,075,658 B2 | 7/2006 | Izatt et al. | |
| 7,140,730 B2 | 11/2006 | Wei et al. | |
| 7,241,286 B2 | 7/2007 | Atlas | |
| 7,261,687 B2 | 8/2007 | Yang | |
| 7,349,098 B2 | 3/2008 | Li | |
| 7,364,543 B2 | 4/2008 | Yang et al. | |
| 7,366,376 B2 | 4/2008 | Shishkov et al. | |
| 7,428,053 B2 | 9/2008 | Feldchtein et al. | |
| 7,450,244 B2 | 11/2008 | Xie | |
| 7,460,248 B2 | 12/2008 | Kurtz et al. | |
| 7,480,058 B2 | 1/2009 | Zhao et al. | |
| 7,538,886 B2 | 5/2009 | Feldchtein | |
| 7,538,940 B2 | 5/2009 | Merz | |
| 7,544,162 B2 | 6/2009 | Ohkubo | |
| 7,549,747 B2 | 6/2009 | Nawata et al. | |
| 7,551,817 B2 | 6/2009 | Teramura | |
| 7,554,669 B2 | 6/2009 | Buckland et al. | |
| 7,554,723 B2 | 6/2009 | Moeller et al. | |
| 7,564,565 B2 | 7/2009 | Shimizu et al. | |
| 7,564,568 B2 | 7/2009 | De Groot et al. | |
| 7,567,349 B2 | 7/2009 | Tearney et al. | |
| 7,567,596 B2 | 7/2009 | Dantus et al. | |
| 7,576,865 B2 | 8/2009 | Chen et al. | |
| 7,625,366 B2 | 12/2009 | Atlas | |
| 7,728,985 B2 | 6/2010 | Feldchtein et al. | |
| 7,796,243 B2 | 9/2010 | Choo-Smith et al. | |
| 7,805,034 B2 | 9/2010 | Kato et al. | |
| 7,821,643 B2 | 10/2010 | Amazeen et al. | |
| 7,894,046 B2 | 2/2011 | Morofke et al. | |
| 7,944,566 B2 | 5/2011 | Xie | |
| 7,952,718 B2 | 5/2011 | Lie et al. | |
| 8,169,618 B2 | 5/2012 | Inoue | |
| 8,174,702 B2 | 5/2012 | Tearney et al. | |
| 8,259,303 B2 | 9/2012 | Johnson et al. | |
| 8,285,368 B2 | 10/2012 | Chen et al. | |
| 8,345,257 B2 | 1/2013 | Bonnema et al. | |
| 2003/0100824 A1 | 5/2003 | Warren et al. | |
| 2005/0196324 A1 | 9/2005 | Harris et al. | |
| 2007/0081166 A1 | 4/2007 | Brown et al. | |
| 2009/0141237 A1 | 6/2009 | Izatt et al. | |
| 2011/0279821 A1 | 11/2011 | Brennan et al. | |
| 2011/0282190 A1 | 11/2011 | Caffey et al. | |
| 2011/0282191 A1 | 11/2011 | Brennan et al. | |
| 2011/0282331 A1 | 11/2011 | Brennan et al. | |
| 2012/0283804 A1 | 11/2012 | Kang et al. | |
| 2012/0330101 A1 | 12/2012 | Brennan et al. | |
| 2012/0330102 A1 | 12/2012 | Brennan et al. | |

FOREIGN PATENT DOCUMENTS

| | | |
|---|---|---|
| WO | 2006004743 | 1/2006 |
| WO | 2008045851 | 4/2008 |
| WO | 2009094341 | 7/2009 |
| WO | 2010104752 | 9/2010 |

OTHER PUBLICATIONS

VivoSight OCT Scanner; Michelson Diagnostics Limited; http://www.md-ltd.co.uk/; information available prior to May 31, 2011.

SDOCT System; Bioptigen, Inc.; http://www.bioptigen.com; information available prior to May 31, 2011.

Niris; Imalux, Inc.; http://www.imalux.com/; information available prior to May 31, 2011.

Larin, K., et al., "Assessing molecular diffusion in tissues using optical coherence tomography," SPIE press release (Jun. 28, 2008), http://spie.org/x25484.xml?ArticleID=x25484.

Boppart, S., "High-Resolution Optical Coherence Tomography-Guided Laser Ablation of Surgical Tissue", Journal of Surgical Research 82, 275-284 (1999), http://biophotonics.illinois.edu/publications/biophotonics_current/highresolutionoctguidedlaserablation.pdf.

Zhong, H., et al., Biophotonics, Nanophotonics and Metamaterials, 2006, pp. 84-87, website: http://ieeexplore.ieee.org/xpl/freeabs_all.jsp?tp=&arnumber=4134743&isnumber=4095340.

Margallo-Balbas, E. et al., "Thermo-optical delay line for optical coherence tomography," Proc. SPIE, vol. 6717, 671704 (2007).

Research and Markets: Strategic Analysis of Optical Imaging Technologies in U.S. Clinical Diagnostics and Drug Discovery Markets, Jun. 4, 2009, website: http://www.tradingmarkets.com/.site/news/Stock%20News/2359815/ (accessed Aug. 3, 2009).

Frost and Sullivan Report (subscription required), U.S. Optical Imaging Technologies to Benefit from Technical Advances and Rising Uptake in Certain Application Areas, Jun. 19, 2009, (accessed Jul. 26, 2009).

Smolka, G. Optical Coherence Tomography: Technology, Markets, and Applications 2008-2012, PennWell Corp., website: http://www.laserfocusworld.com/articles/318570 (accessed Jul. 27, 2009).

OSE-1800; Shenzhen Moptim Imaging Technique Co.,Ltd; Moptim website: http://www.moptim.cn/liste.asp?ProdId=0002; information available prior to May 31, 2011.

SOCT Copernicus HR; Optopol Technology; Optopol webite: http://optopol.com/en/index.php?option=com_content&task=view&id=155&Itemid=127; information available prior to May 31, 2011.

SS-1000 Ophthalmic 3D High-Speed swept-source OCT System; Tomey; Tomey website: http://www.tomey.de/index.php?option=com_content&view=article&id=86&Itemid=81&lang=en; information available prior to May 31, 2011.

Topcon 3D OCT-1000; Topcon Medical; Topcon medical website: http://www.topconmedical.com/products/index.cfm; information available prior to May 31, 2011.

Zeiss Visante OCT; Carl Zeiss Meditec; Carl Zeiss Visante website: http://www.meditec.zeiss.com/visante; information available prior to May 31, 2011.

RTVue; Optovue; Optovue website: http://www.optovue.com/products/rtvue; information available prior to May 31, 2011.

Cirrus HD-OCT system; Carl Zeiss Meditech; Carl Zeiss website: http://www.meditec.zeiss.com/88256DE3007B916B/0/CE41686BA660687CC1257331003A024D/$file/cirrus_brochure.pdf (accessed Jul. 31, 2009).

"Ultra High-Resolution Optical Coherence Tomography for Ocular Imaging of Small Animals," 25th Southern Biomedical Engineering Conference 2009 website: http://www.springerlink.com/content/v63r4l03278256v1/ (accessed Jul. 31, 2009).

Zhou, C. et al., "Dual channel dual focus optical coherence tomography for imaging accommodation of the Eye", Optics Express, vol. 17, No. 11 (May 25, 2009).

Han, S. et al., "Handheld forward-imaging needle endoscope for ophthalmic optical coherence tomography inspection," J. Biomed. Opt., vol. 13 (Apr. 21, 2008).

"In vivo 3-D imaging of gastrointestinal tracts by use of an endoscopic swept source optical coherence tomography with a microelectromechanical endoscopic rotational probe," Proc SPIE website: http://spiedl.aip.org/getabs/servlet/GetabsServlet?prog=normal&id=PSISDG006847000000168472Y000001&idtype=cvips&gifs=yes (accessed Jul. 31, 2009).

Schuman, J. S., "Spectral Domain Optical Coherence Tomography for Glaucoma," Trans. Am. Ophthalmol. Soc. vol. 106 (2008).

Advances in Optical Imaging (Technical Insights) Frost and Sullivan Report (subscription required), published Dec. 31, 2007, (accessed Jul. 31, 2009).

(56) References Cited

OTHER PUBLICATIONS

Frost & Sullivan Lauds Carl Zeiss Meditec for Dominating the OCT Market for Ophthalmic Applications Frost and Sullivan Report (subscription required), published Mar. 31, 2009, (accessed Jul. 31, 2009).
Ophthalmic Optical Coherence Tomography Market: Past, Present, & Future Optical Coherence Tomography News (Mar. 29, 2009) Ophthalmology http://www.octnews.org/articles/1027616/ophthalmic-optical-coherence-tomography-market-pas/ (accessed Jul. 31, 2009).
Frost and Sullivan Report (subscription required) Strategic Analysis of Optical Imaging Technologies in U.S. Clinical Diagnostics and Drug Discovery Markets, Mar. 24, 2009.
Sayeram, S. et al., "High-resolution SDOCT imaging—cutting-edge technology for clinical and research applications," Biophotonics, Photonik International Online, Nov. 2008 (originally published in German in Photonik Mar. 2008).
Fercher, A.F. et al. "Optical coherence tomography—principles and applications," Reports on Progress in Physics, Institute of Physics Publishing, vol. 66, pp. 239-303 (Jan. 20, 2003).
Nickles Fader, A. et al., "Laparoendoscopic single-site surgery (LESS) in gynecologic oncology: Technique and initial report", Gynecologic Oncology, vol. 114, pp. 157-161, (May 28, 2009).
Miniature Non-MEMS Scanner; Electro-Optical Products Corporation; information available prior to May 31, 2011.
Miller, K. et al., "A new follicle aspiration needle set is equally effective and as well tolerated as the standard needle when used in a prospective randomized trial in a large in vitro fertilization program." Fertility and sterility. Jan. 2004 81 (1) pp. 191-193.
Wikipedia website http://en.wikipedia.org/wiki/Needle_gauge_comparison_chart; information available prior to May 31, 2011.
OCTS Spectral Engine DeepView™ 800-Series; BaySpec, Inc.; Bay Spec website: http://www.bayspec.com/userfiles/file/BaySpec-Datasheet%20-%20OCTS-800.pdf; information available prior to May 31, 2011.
The EX1301 OCT Microscope and VivoSight OCT Scanner; Michelson Diagnostics Limited; Michaelson Diagnostics website: http://www.md-ltd.co.uk/vivosight.html; information available prior to May 31, 2011.
Spectral Radar and Swept Source OCT Systems; Thorlabs; Thorlabs website: http://www.thorlabs.com/newgrouppage9.cfm?objectGroup_ID=2005; information available prior to May 31, 2011.
"Laparoscopic optical coherence tomography imaging of human ovarian cancer.," Press Release Jun. 2009, website: http://www.octnews.org/articles/1268184/feature-of-the-week-62109-laparoscopic-optical-coh/.
"A prototype hybrid intraoperative probe for ovarian cancer detection," Optical Society of America website: http://www.opticsinfobase.org/DirectPDFAccess/A83B7572-BDB9-137E-C78DECA11F3DBBB7__179197.pdf?da=1&id=179197&seq=0&CFID=49726490&CFTOKEN=33970962 (accessed Jul. 23, 2009).
"Hand-held in vivo optical coherence tomography (OCT) probe," BioOptics World website: http://www.biioopticsworld.com/display_article/340111/131/ARTCL/none/Depar/DIAGNOSTIS-AND-TREATMENT:-Funding-to-further-bio-optics-product?dcmp=rss; information available prior to May 31, 2011.
Evans, C. et al., "In vitro ovarian tumor growth and treatment response dynamics visualized with time-lapse OCT imaging," Optics Express, vol. 17, Issue 11, pp. 8892-8906 (May 12, 2009); website: http://www.opticsinfobase.org/abstract.cfm?URI=oe-17-11-8892.
"Advanced Cancer Research Using Next-Generation Medical Imaging with PXI Modular Instrumentation and NI LabVIEW," National Instruments website: http://sine.ni.com/cs/app/doc/p/id/cs-11321 (accessed Jul. 26, 2009).
Frost and Sullivan Report (subscription required), U.S. Medical Devices Market Outlook, Feb. 2008 (accessed Jul. 27, 2009).
Frost and Sullivan Report (subscription required), Developments in Tomography Technologies, Dec. 2007 (accessed Jul. 27, 2009).
Laparoscopic optical coherence tomography imaging of human ovarian cancer, Optical Coherence Tomography News (Jun. 20, 2009) website: http://www.octnews.org/articles/1268184/feature-of-the-week-62109-laparoscopic-optical-coh/ (accessed Jul. 27, 2009).
Lee, C. M. et al., "Scanning fiber endoscopy with highly flexible, 1 mm catheterscopes for wide-field full-color imaging," J. Biophoton., 3, No. 5-6, pp. 385-407 (Mar. 25, 2010).
PCT Search Report and Written Opinion for PCT/US2011/038593 dated Feb. 8, 2012.
Joos KM et al., "Free electron laser (FEL) laser-tissue interaction with human cornea and optic nerve," SPIE Proceedings of Ophthalmic Technologies (VI), 2673, 89-92 (1996).
Shen J et al., "Cultured human cornea healing process after free electron laser ablation," SPIE Proceedings of Ophthalmic Technologies VII: vol. 2971, 83-87 (1997).
Joos K et al., "Free electron laser effects upon fibrin tissue glue: a preliminary study," SPIE Proceedings of Ophthalmic Technologies X, vol. 3908, 132-137 (2000).
Joos K et al., "Acute optic nerve sheath fenestration in humans using the free electron laser (FEL): a case report," SPIE Proceedings of Ophthalmic Technologies XII, vol. 4611, 81-85 (2002).
Edwards G et al., "Comparison of OPA and Mark-III FEL for tissue ablation at 6.45 microns," SPIE Proceedings of Commercial and Biomedical Applications of Ultrafast and Free-Electron Lasers, vol. 4633, 194-200 (2002).
MacKanos MA et al., "Fiber-delivered mid-infrared (6-7 µM) laser ablation of retinal tissue under perfluorodecalin," SPIE Proceedings of Ophthalmic Technologies XIII-BIOS, vol. 4951, 83-91 (2003).
Joos K et al., "Attenuation of midinfrared free electron laser energy with eyewear," SPIE Ophthalmic Technologies XV-BIOS, vol. 5688, 170-176 (2005).
MacKanos MA et al., "Corneal ablation using the pulse stretched free electron laser," SPIE Ophthalmic Technologies XV-BIOS, vol. 5688, 177-184 (2005).
Joos K et al., "Endoscopic-Approach Development for Minimally Invasive Orbital Surgery," SPIE Ophthalmic Technologies XVII-BIOS, 2, vol. 6426-48, 1-8 (2007).
Joos K et al., "Experimental retinectomy with a 6.1 µm Q-switched Raman-shifted alexandrite laser," SPIE Ophthalmic Technologies XX-BIOS, vol. 7550-33, 1-3 (2010).
Sun W et al., "Endoscopic goniotomy with the free electron laser in congenital glaucoma rabbits," Journal of Glaucoma, 9:325-333 (2000).
Joos K et al., "Optic nerve sheath fenestration with a novel wavelength produced by the free electron laser (FEL)," Lasers in Surgery and Medicine, 27:191-205 (2000).
Shen J et al., "Hollow-glass waveguide delivery of an infrared free-electron laser for microsurgical applications," Applied Optics: Optical Technology and Biomedical Optics, 40:583-587 (2001).
Joos KM et al., "Chronic and acute analysis of optic nerve sheath fenestration with the free electron laser in monkeys," Lasers in Surgery and Medicine, 32:32-41 (2003).
Edwards GS et al., "Free-electron-laser-based biophysical and biomedical instrumentation," Review of Scientific Instruments, 74:3207-3245 (2003).
Mawn LA et al., "Development of an orbital endoscope for use with the free electron laser," Ophthalmic Plastic and Reconstructive Surgery, 20:150-157 (2004).
MacKanos MA et al., "The effect of free-electron laser pulse structure on mid-infrared soft-tissue ablation: biological effects," Physics in Medicine and Biology: 50: 1885-1899 (2005).
Joos KM et al., "Optic nerve sheath fenestration with endoscopic accessory instruments versus the free electron laser (FEL)," Lasers in Surgery and Medicine 38:846-51 (2006).
MacKanos M et al., "Mid infrared optical parametric oscillator (OPO) as a viable alternative to tissue ablation with the free electron laser (FEL)," Lasers in Surgery and Medicine, 39:230-236 (2007).

(56) References Cited

OTHER PUBLICATIONS

Shah RJ et al., "Endoscopic Free Electron Laser Technique Development for Minimally Invasive Optic Nerve Sheath Fenestration," Lasers in Surgery and Medicine, 39:589-596 (2007).

Kozub J et al., "Raman-shifted alexandrite laser for soft tissue ablation in the 6- to 7-μm wavelength range," Biomedical Optics Express, 2, (5):1275-1281 (2011). http://www.opticsinfobase.org/abstract.cfm?URI=boe-2-5-1275.

Joos K et al., "A miniature forward-imaging optical coherence tomography probe," SPIE Ophthalmic Technologies XXII-BIOS (2012); vol. 8209-34, 1-7.

Joos KM et al., "Miniature real-time intraoperative forward-imaging optical coherence tomography probe," Biomedical Optics Express, 4(8):1342-50 (2013).

Shen JH et al., "An Intraocular OCT Probe," The Association for Research in Vision and Ophthalmology, Presentation Abstract (May 2, 2011).

Yong Huang and Jin U. Kang, "Corneal Tissue Ablation using 6.1 μm quantum cascade laser," Proceedings of SPIE, vol. 8209 (2012).

Yong Huang and Jin U. Kang, "Quantum cascade laser thermal therapy guided by FDOCT," Chinese Optics Letters, col. 11(1), 011701 (2013) (posted online Dec. 26, 2012).

\* cited by examiner

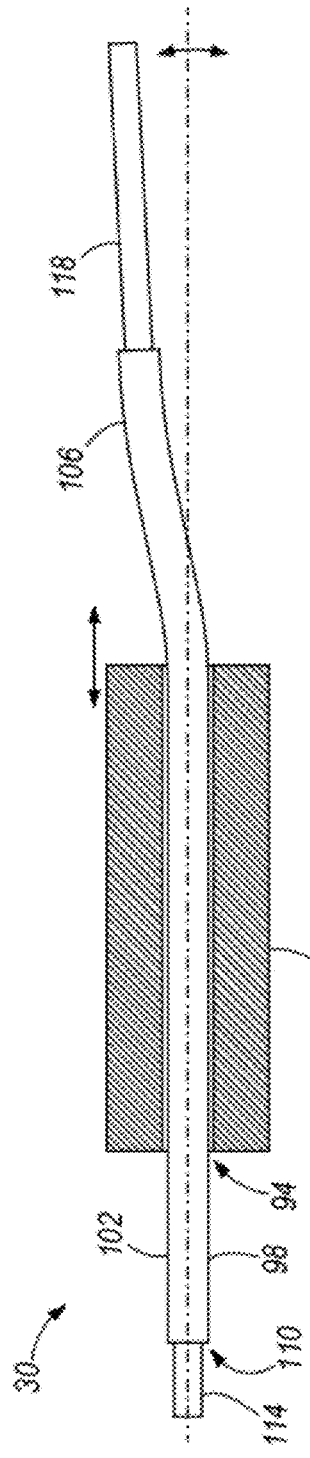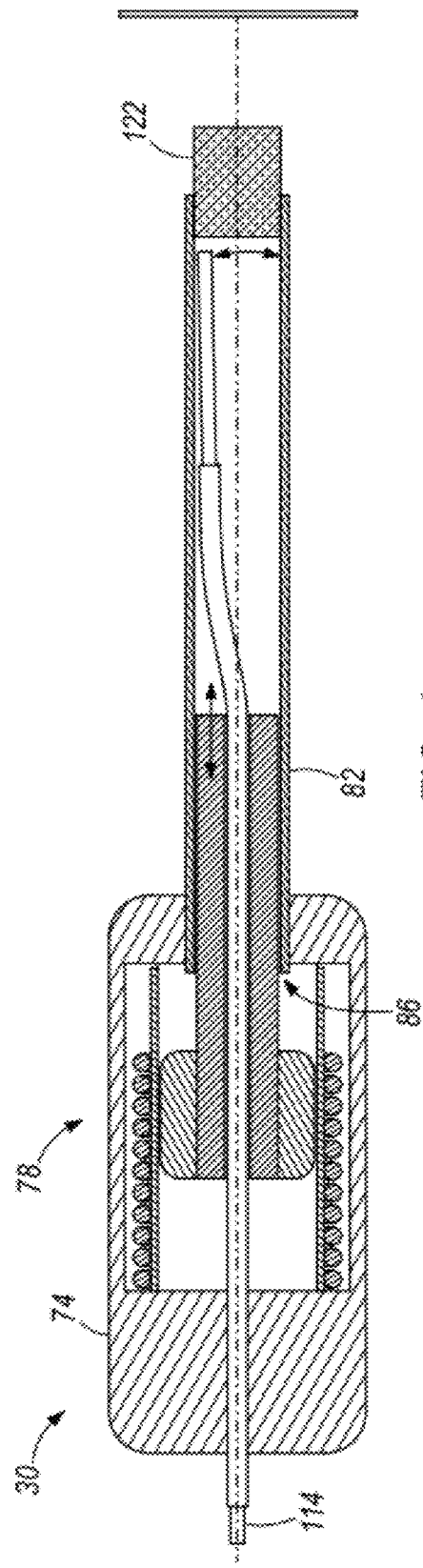

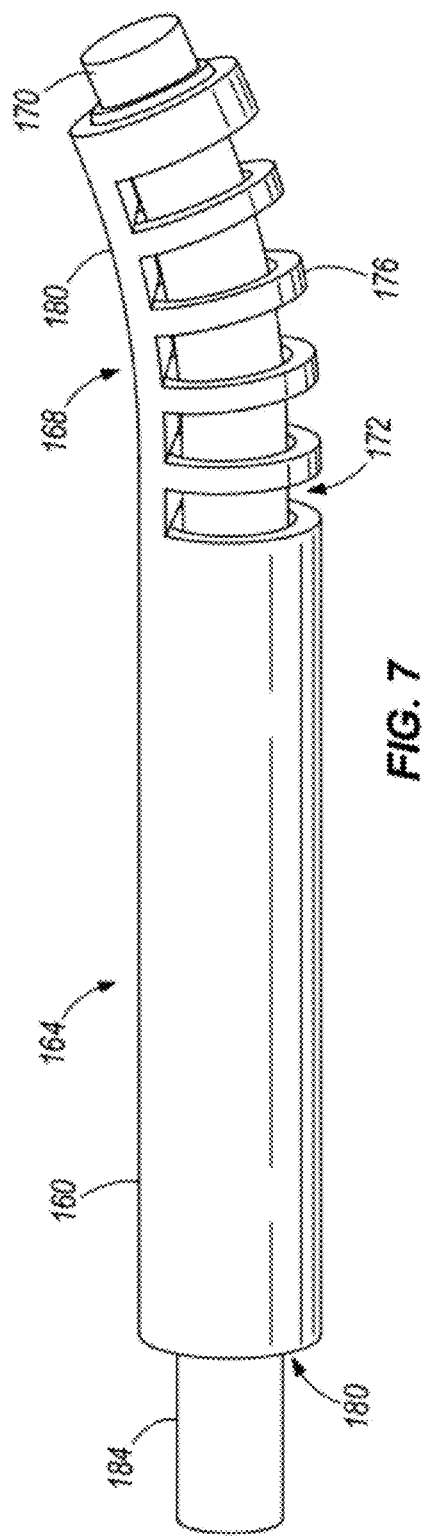
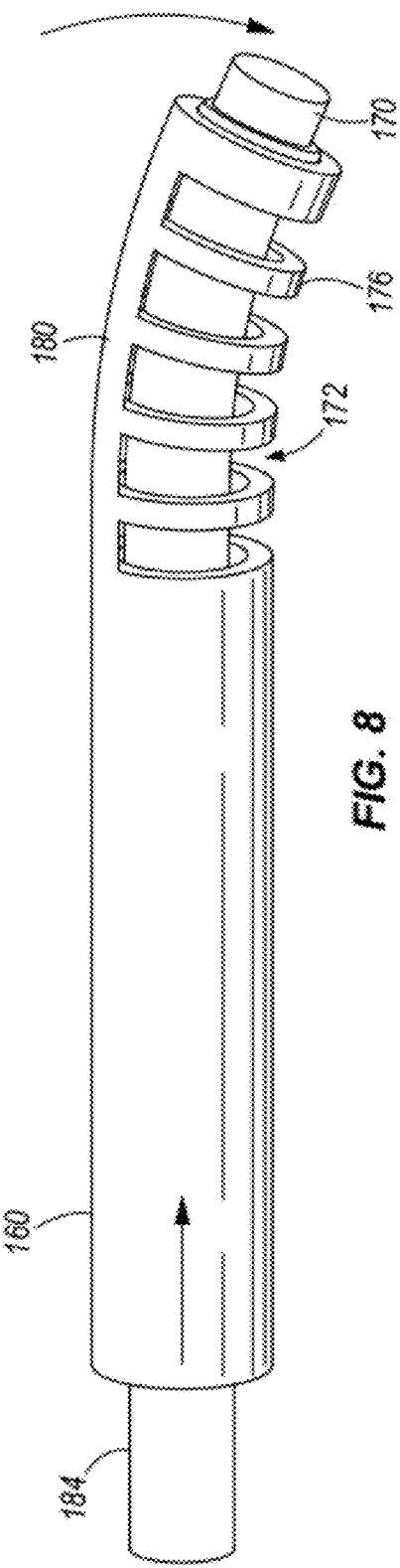
FIG. 7
FIG. 8

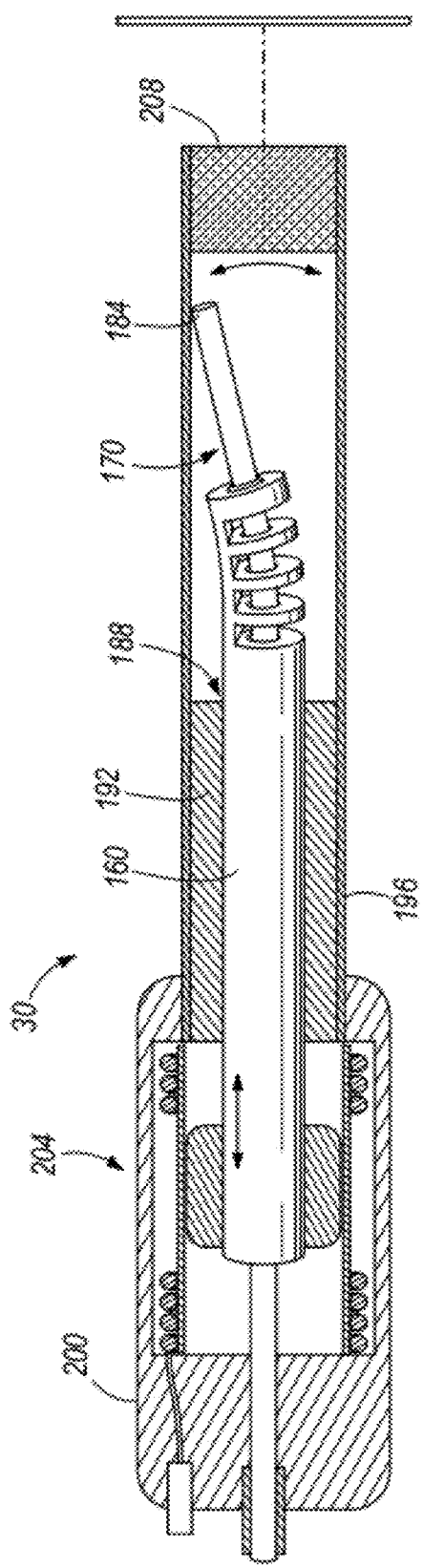
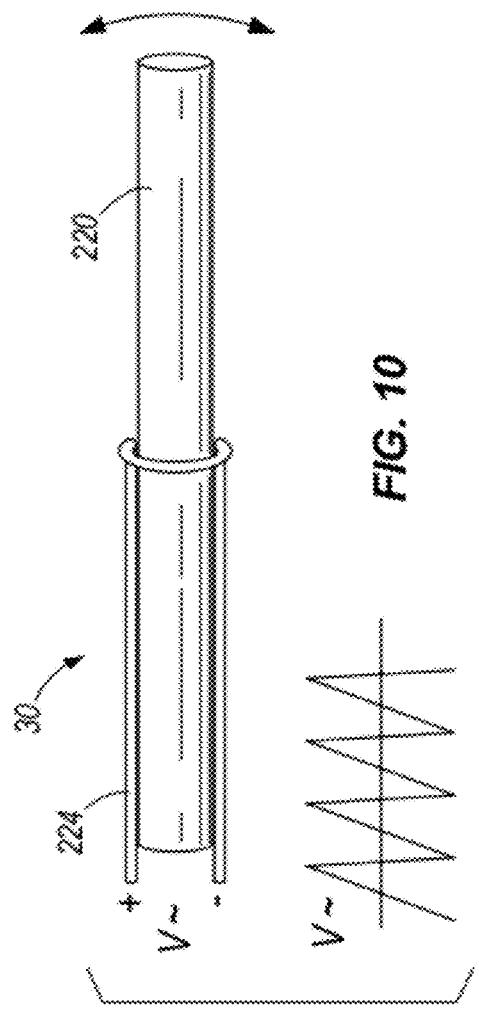
FIG. 9
FIG. 10

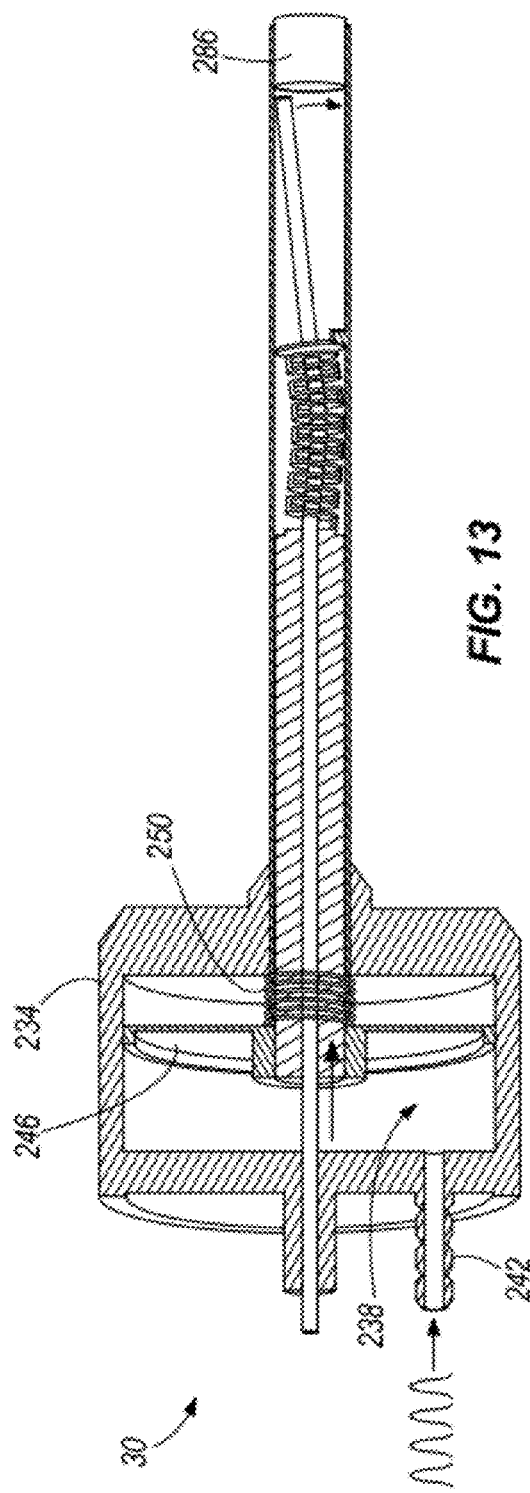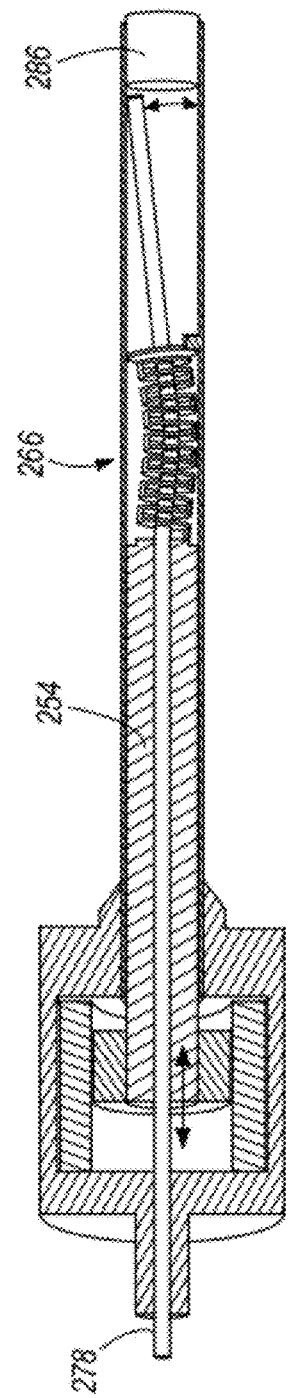

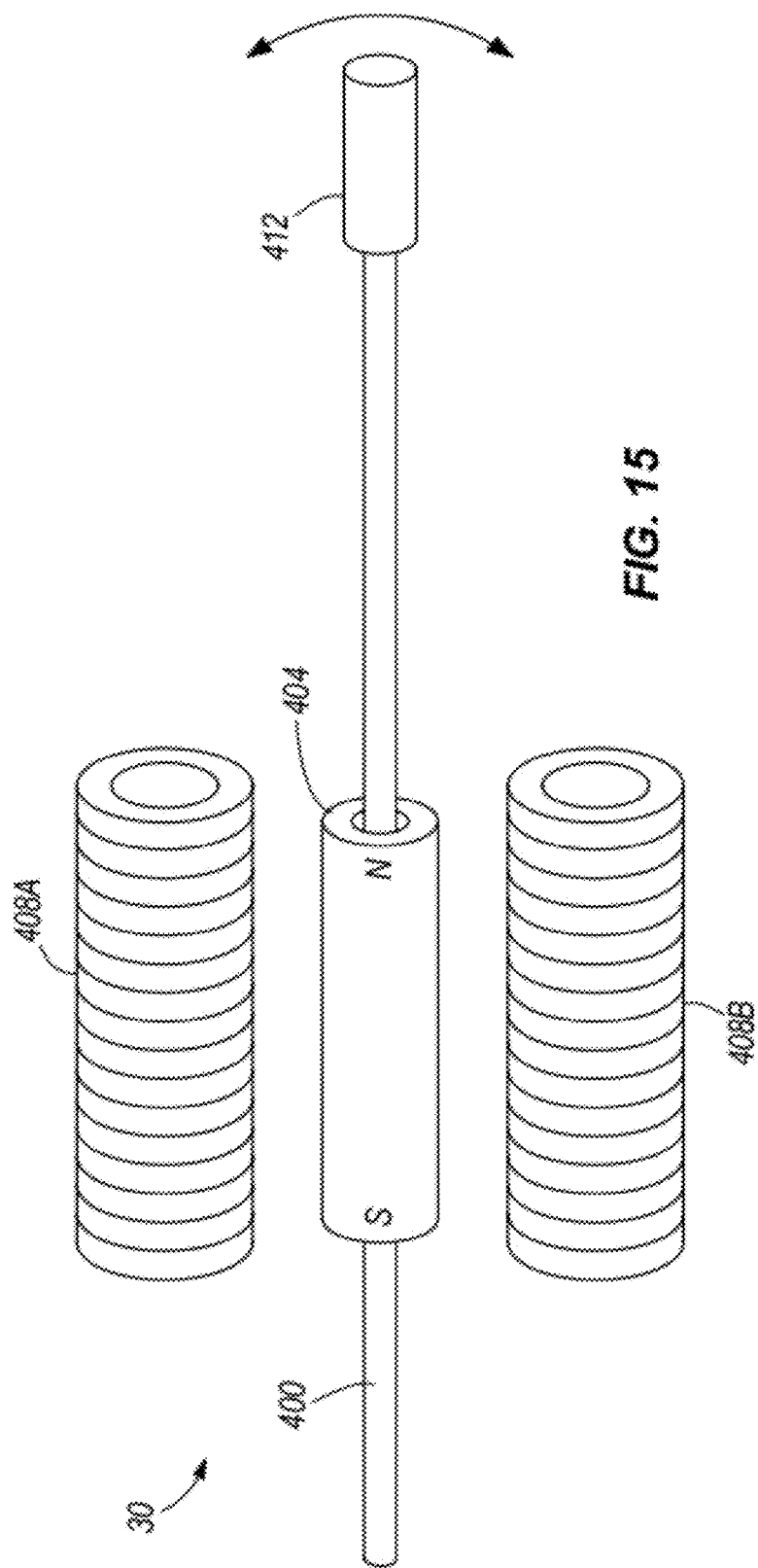

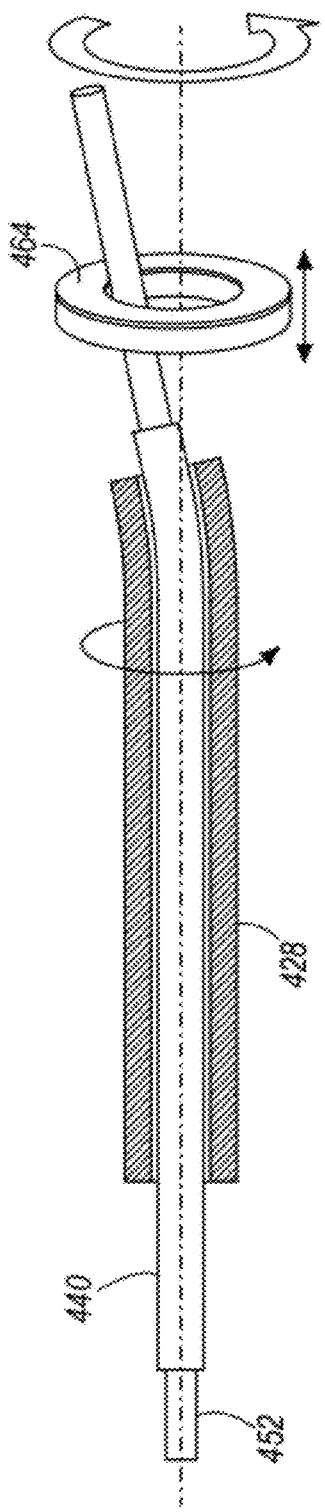
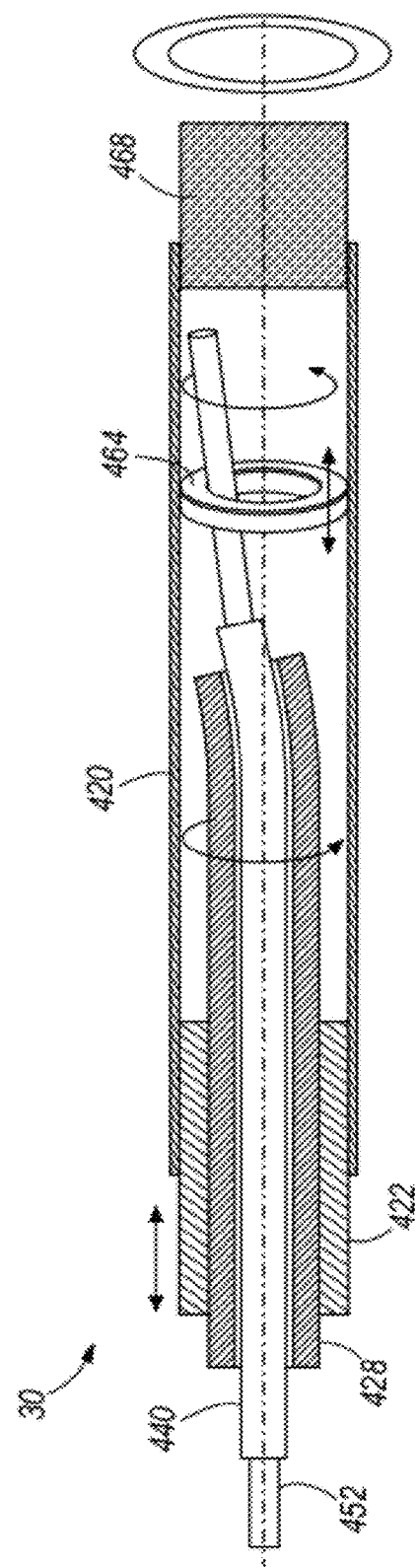

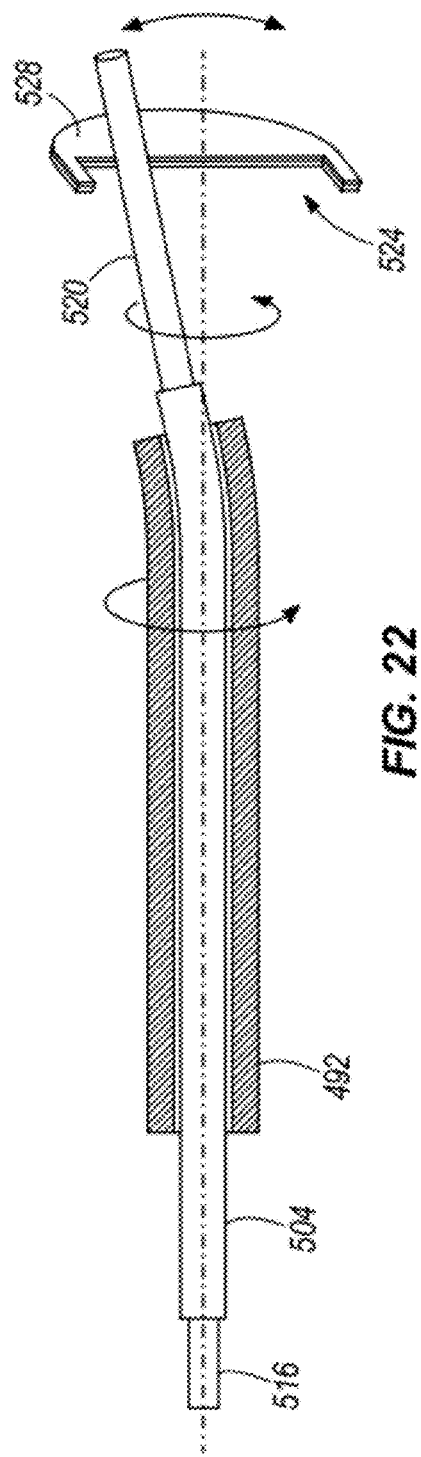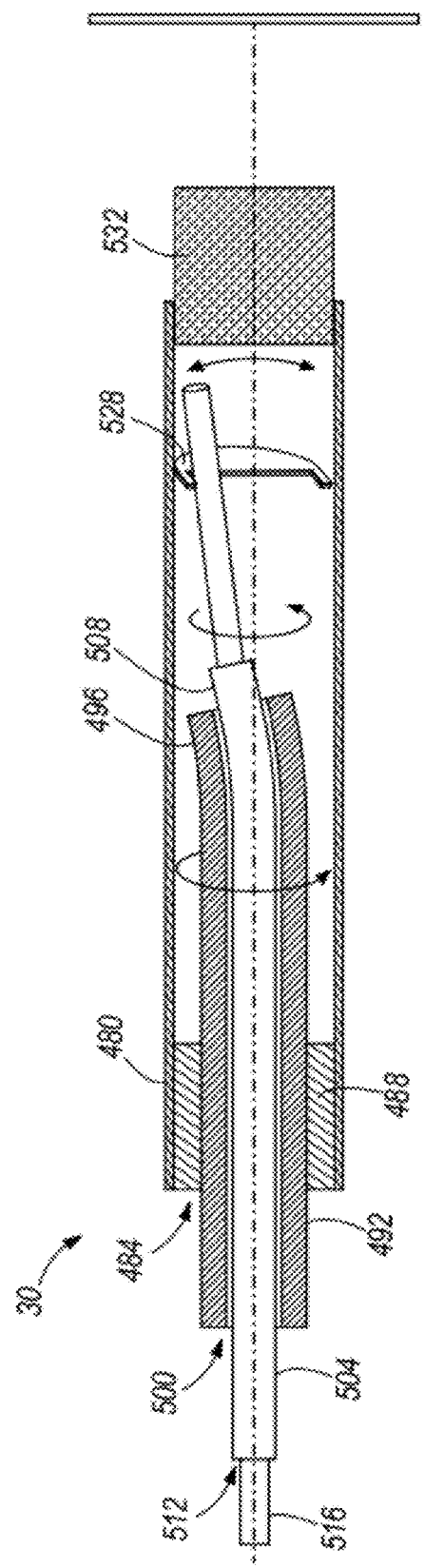

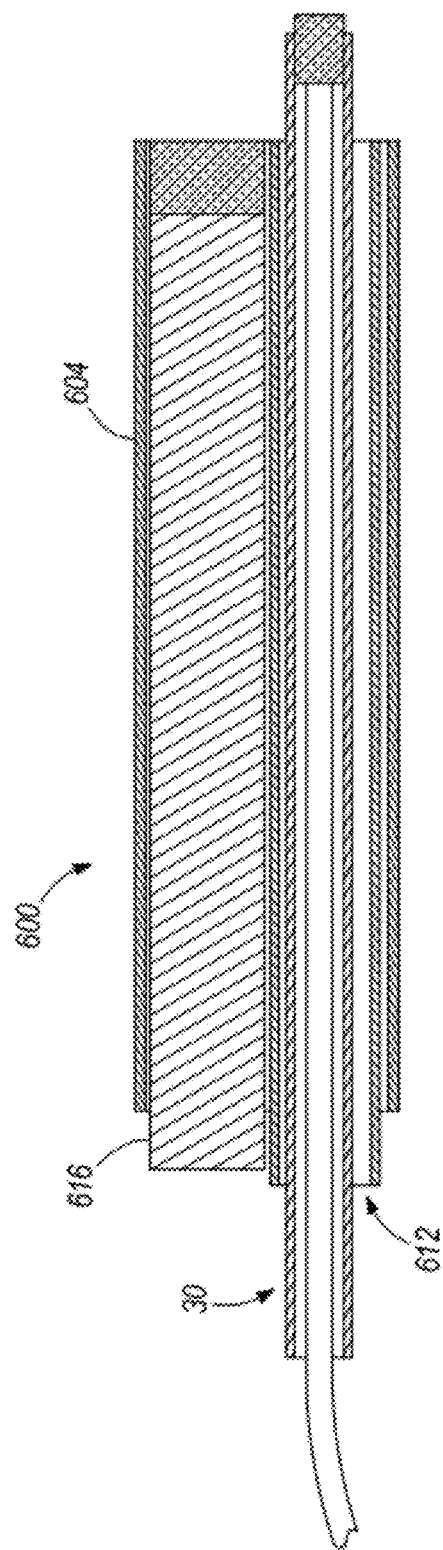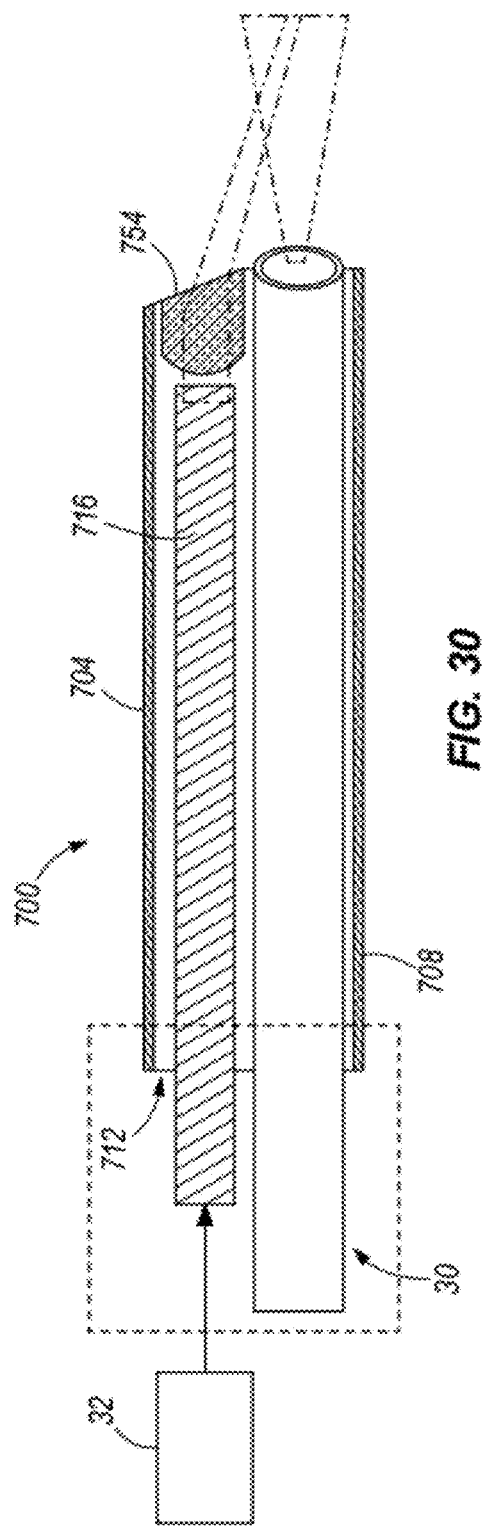

APPARATUS AND METHOD FOR REAL-TIME IMAGING AND MONITORING OF AN ELECTROSURGICAL PROCEDURE

STATEMENT REGARDING FEDERALLY SPONSORED RESEARCH OR DEVELOPMENT

This invention was made with government support under grant R21 5R21EY19752 awarded by the National Institutes of Health and under FA9550-04-1-0045 awarded by the Air Force Office of Scientific Research—DOD. The government has certain rights in the invention.

BACKGROUND OF THE INVENTION

Advances in Optical Coherence Tomography (OCT) technology have made it possible to use OCT in a wide variety of applications. One application of OCT is in ophthalmology for imaging eye diseases due to the high transmittance of ocular media. OCT technology was invented in the early 1990's to generate depth-resolved images of tissue level microstructures, in vivo, and without physical contact. Second generation imaging technology, such as frequency-domain, swept-source, and spectral-domain OCT, has improved the signal-to-noise ratio over first generation technology, translating to faster imaging. As a result of this speed increase, high resolution cross-sectional images (B-scans) can be acquired at video-rates and three-dimensional images can be acquired very quickly. Sunita Sayeram and Joseph Izatt, "High-resolution SDOCT imaging—cutting-edge technology for clinical and research applications," Photonik (November 2008) (hereinafter referred to as the "Photonik Article").

As noted in the Photonik Article, OCT is an imaging technique which provides microscopic tomographic sectioning of biological samples. By measuring singly backscattered light as a function of depth, OCT fills a valuable niche in imaging of tissue ultrastructure, providing sub-surface imaging with high spatial resolution (~5-10 µm) in three dimensions and high sensitivity (>110 dB) in vivo with no contact needed between the probe and the tissue.

In biological and biomedical imaging applications, OCT allows for micrometer-scale imaging non-invasively in transparent, translucent, and highly-scattering biological tissues. As illustrated in FIG. 1, the longitudinal ranging capability of OCT is based on low-coherence interferometry, in which light from a broadband source is split between illuminating the sample of interest and a reference path in a fiber optic interferometer. The interference pattern of light backscattered from the sample and light from the reference delay contains information about the location and scattering amplitude of the scatterers in the sample. This information is recorded as a map of the reflectivity of the sample versus depth, called an A-scan.

For two or three-dimensional OCT imaging, multiple A-scans are acquired while the sample beam is scanned laterally across the tissue surface, building up a map of reflectivity versus depth and one or two lateral dimensions. The lateral resolution of the B-scan is given by the confocal resolving power of the sample arm optical system.

Ophthalmology has embraced minimally-invasive surgery since 1956 when the high-pressure xenon-arc lamp became commercially available for photocoagulation. This device has been replaced by various lasers developed over the years. As a result, laser procedures have tremendously advanced and improved vision outcomes in all segments of ophthalmic surgery.

The Mark-III FEL at Vanderbilt University operates in the 2-10 µm region with a 5 µsec macropulse containing a train of 1-ps micropulses at 3 GHz permitting wavelength selection for specific laser-tissue interactions. It has been determined that a wavelength of 6.1 µm or 6.4 µm produced by the FEL is capable of ablating tissue with a minimal amount of collateral damage, which is desirable for incisions of tissue. Tissues which have been examined with this wavelength include articular cartilage, fibro-cartilage, skin, cornea, and optic nerve sheath. The infrared energy can be delivered through small hollow-glass waveguides to permit the development of microsurgical and minimally invasive procedures. Other laser procedures are performed with conventional lasers with energy directed through laser fibers. An incising instrument would become more clinically valuable if the depth of the incision could be carefully monitored and controlled.

SUMMARY OF THE INVENTION

OCT technology has had a profound effect upon ophthalmic imaging and diagnosis. Its capabilities are also being embraced by gastroenterology, urology, oncology, and other specialties. The OCT B-scan is used daily in ophthalmology clinics to evaluate the delicate structures within the eye for evidence of macular edema, macular holes, subtle retinal lesions, glaucomatous retinal nerve fiber thinning, etc. As noted in the Photonik Article, OCT has evolved with improved imaging speed and resolution especially of the retinal layers in research investigations.

Real-time OCT B-scan imaging of laser ablation has been achieved with ultrahigh-speed optical frequency domain imaging, but not through a miniature probe. Large and small OCT side-scanning probes have been developed to examine tissues within tubular structures such as the esophagus and coronary arteries with lateral resolution up to 10 µm. Probes as small as 0.36 mm have been developed, but they project views only from the side rather than directly in front of the catheter tip. OCT has been combined with the operating microscope, but its lateral resolution was found to be 5-times less than with the handheld OCT probe system during laryngoscopy. A forward-imaging OCT B-scan device has been used to image bladders, but its diameter is relatively large at 5.8 mm×3 mm. The standard microelectromechanical system (MEMS) scanning mirror component of an OCT forward-imaging probe has been reduced to a diameter of 1 mm, but the mirror alone is still larger than ophthalmic probe requirements. Others have used a piezoelectric cantilever system with a rod lens 2.7 mm in diameter, a lead zirconate titanate actuator and cantilever within a 2.4 mm diameter probe, a fiber-bundle system measuring 3.2 mm in diameter, complicated paired rotating GRIN lenses in a probe measuring 1.65 mm in diameter, and an electrostatic scanning probe measuring 2.2 mm in diameter. To pass through the 1.2 mm diameter size of the smallest endoscopic working channel, a novel design is required. Individual OCT A-scan components alone would permit miniaturization of the sensing probe, but the system would be unable to provide two-dimensional information. Alternative designs for permitting scanning within a miniature probe are required to break the 1.2 mm diameter size barrier.

Real-time OCT imaging of laser ablation has been achieved in an external imaging system and through one large probe, but not through a miniature forward-imaging probe. Most studies have used OCT to examine the tissues after the laser procedures have been completed rather than real-time during the actual lasing. Real-time monitoring of an incising laser would be useful in surgeries. We successfully have performed endoscopic optic nerve sheath fenestration, but judgment of the incision depth is challenging. This led to the search for a means to provide real-time z-directional guidance of the incisional depth that a combined laser and OCT probe feasibly could provide to improve endoscopic surgery. Such imaging guidance may be valuable in the development of future robotic surgical techniques.

Accordingly, in one construction, the invention is related to a OCT probe miniaturized for insertion into a working channel of an endoscope for imaging tissue. In another construction, the invention is related to the combination of OCT technology and laser technology that is reduced to a miniature probe that can be inserted into the working channel of an endoscope for detecting incision of a tissue layer as it occurs so that the underlying tissues are protected from injury. High-resolution OCT forward-imaging alone could be used to evaluate sub-surface structures during endoscopic procedures. In addition, it can precisely guide the depth of an endoscopic laser incision with real-time monitoring. This is likely to advance therapies within small spaces, such as the space behind the eye. This endoscopic-capable device has the potential for adoption in multiple surgical specialties with or without the laser.

Other aspects of the invention will become apparent by consideration of the detailed description and accompanying drawings.

BRIEF DESCRIPTION OF THE DRAWINGS

FIGS. 3-4 are schematic illustrations of an OCT probe according to one embodiment of the present invention.

FIGS. 6-9 are schematic illustrations of an OCT probe according to one embodiment of the present invention.

FIG. 10 is a schematic illustration of an OCT probe according to one embodiment of the present invention.

FIGS. 11-14 are schematic illustrations of an OCT probe according to one embodiment of the present invention.

FIGS. 15-16 are schematic view illustrations of an OCT probe according to one embodiment of the present invention.

FIGS. 17-21 are schematic illustrations of an OCT probe according to one embodiment of the present invention.

FIGS. 22-23 are schematic illustrations of an OCT probe according to one embodiment of the present invention.

FIGS. 25-29 are schematic illustrations of an OCT probe according to one embodiment of the present invention positioned within the working channel of an endoscope.

FIGS. 30-31 are schematic top view illustrations of a combined OCT probe and laser device according to one embodiment of the present invention.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

Figure 1:
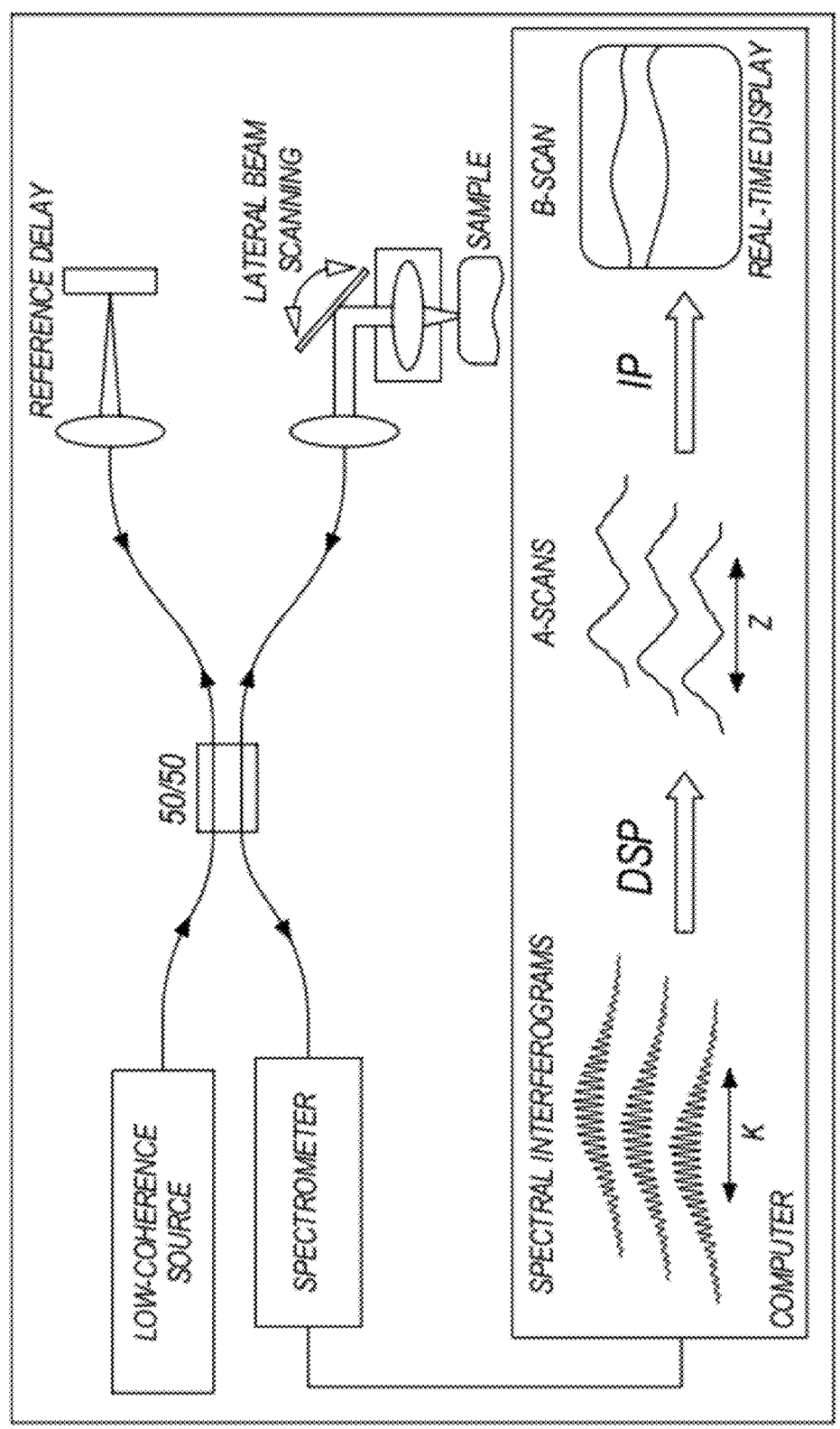
FIG. 1 is a schematic illustration of an OCT system.
Figure 2:
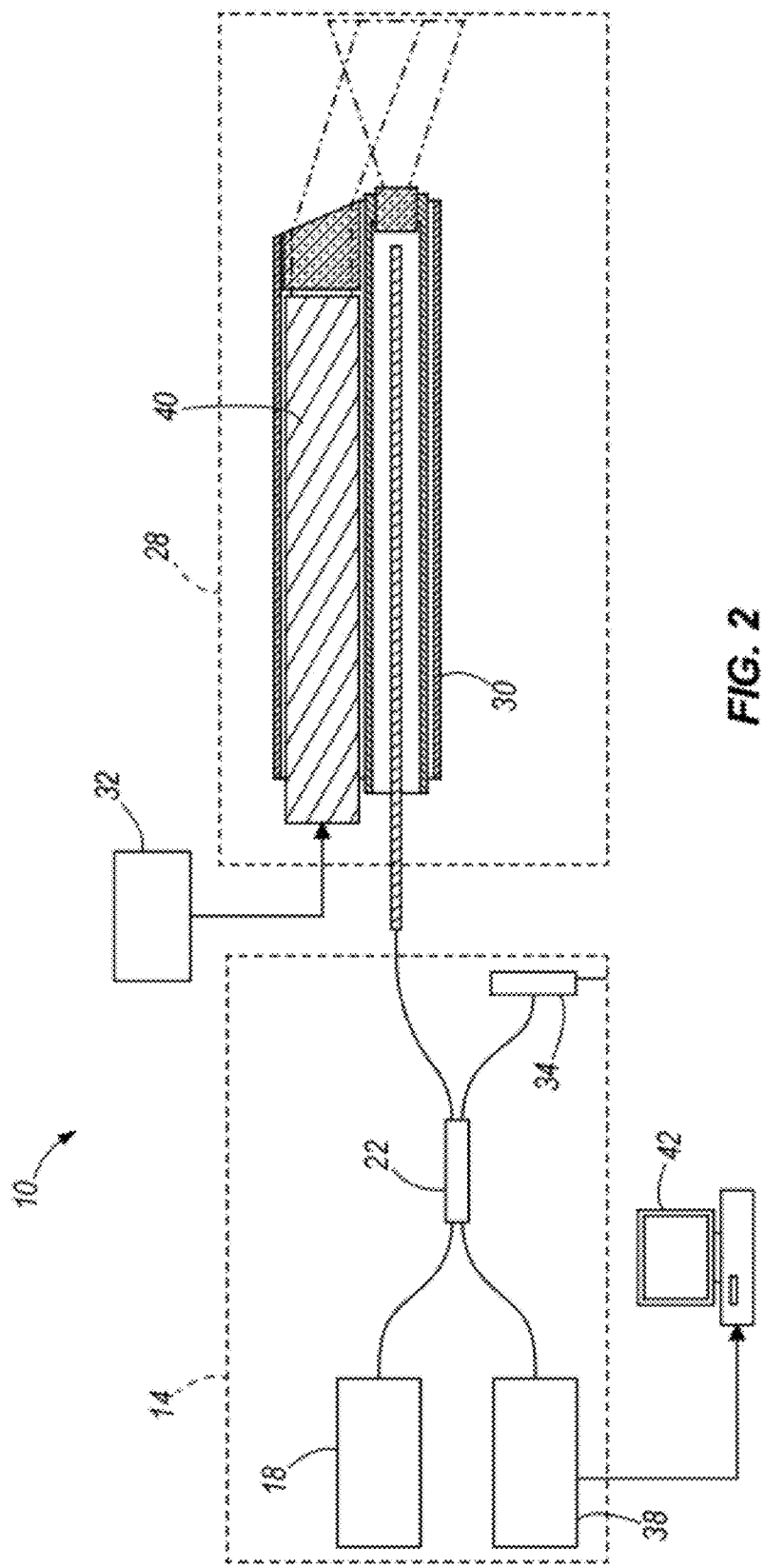
FIG. 2 is a schematic illustration of an OCT system incorporating an OCT probe and laser according to one embodiment of the present invention.

FIG. 2 schematically illustrates an OCT laser system 10 according to one embodiment of the present invention. The OCT laser system 10 includes an OCT system 14, an OCT probe/laser probe system 28, and a treating laser system 32. The OCT system 14 includes a light source 18 that outputs a light signal, which is then input to a beam splitter 22 where the light signal is split between illuminating a sample via an OCT probe 30 and a reference device 34. The reference device 34 can include a lens and a reference mirror. The OCT system 14 also includes a photo detector 38 for receiving backscattered light from the sample that was collected by the OCT probe 30 and light from the reference device 34. The photo detector 38 can convert the light signals to digital signals to generate an OCT image signal, which is transmitted to a computer processor 42 for generation of an image, such as an A-scan or a B-scan. The computer processor 42 can include software (e.g., stored on non-transitory computer-readable medium) for processing the data into an A-scan and/or a B-scan.

The OCT probe/laser probe system 28 includes an OCT probe 30 and a laser probe 40. The OCT probe is coupled to the OCT system 14, and the laser probe 40 is coupled to the treating laser system 32. The OCT probe 30 is a miniature intraoperative probe (e.g., 3 mm or smaller such as 25 gauge) capable of forward imaging with OCT. FIGS. 3-4 illustrate one construction of the OCT probe 30. In this construction, the probe 30 can include a housing 74 having an electromagnetic system 78 (e.g., coil, magnet, and suitable electronic circuitry to activate the coil). The housing 74 is connected to a first tube 82 (or conduit) that defines a first bore 86, which is configured to support a second tube 90. The word tube is used herein to describe various constructions of the probe;

however a tube, as used herein, is a conduit having any cross-sectional shape suitable to the invention. Use of the word tube or conduit shall not limit the shape of the probe to a circular cross-section as other cross-sectional shapes are contemplated by the invention.

The outer diameter of the second tube 90 is less than the inside diameter of the first tube 82 such that the second tube 90 can slide or resonate along a length of the first tube 82 when the electromagnetic system 78 is activated. The second tube 90 defines a second bore 94 configured to receive a third tube 98. As illustrated in FIGS. 3-4, the third tube 98 includes a first portion 102 being substantially straight and a second portion 106 having a somewhat S-shaped curvature. The second portion 106 is at the distal portion of the third tube 98. The first tube 82, the second tube 90, and the third tube 98 can comprise stainless steel or other suitable materials or combinations of materials.

With continued reference to FIGS. 3-4, the third tube 98 includes a third bore 110 configured to receive a fiber 114. A portion 118 of the fiber 114 extends from the distal end of the third tube 98 toward a distal end of the first tube 82. A distal end of the fiber 114 is positioned adjacent a GRIN imaging lens 122, which is connected to the distal end of the first tube 82. The portion 118 of the fiber 114 can move laterally or in the X direction (axes definition and used throughout the specification: the Z axis goes horizontally across the paper, the Y axis goes vertically top to bottom, and the X axis goes into the paper) within the first tube 82 when the second tube 90 is activated and slides within the first tube 82. The first tube 82 can include an index-matching liquid.

Figure 5:
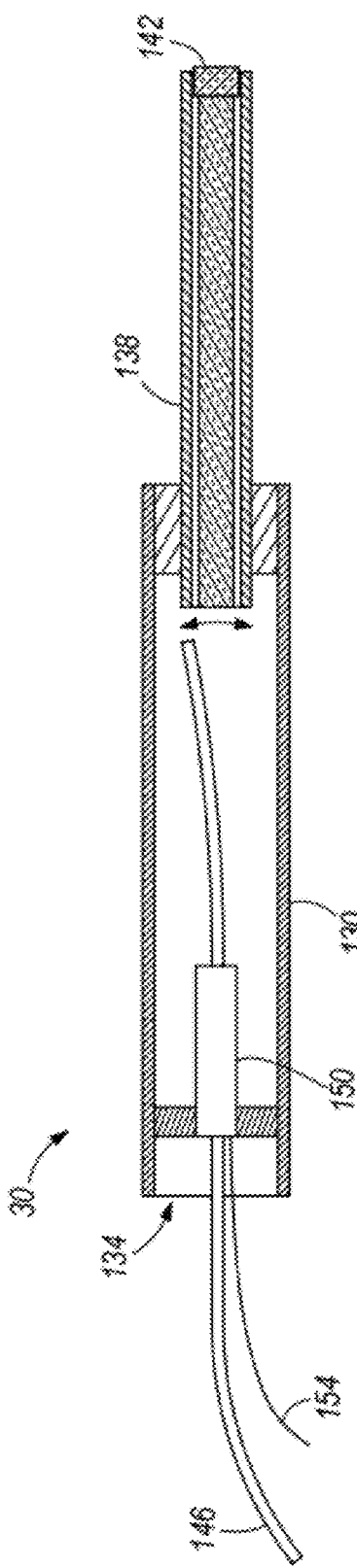
FIG. 5 is a schematic illustration of an OCT probe according to one embodiment of the present invention.
Figure 6:
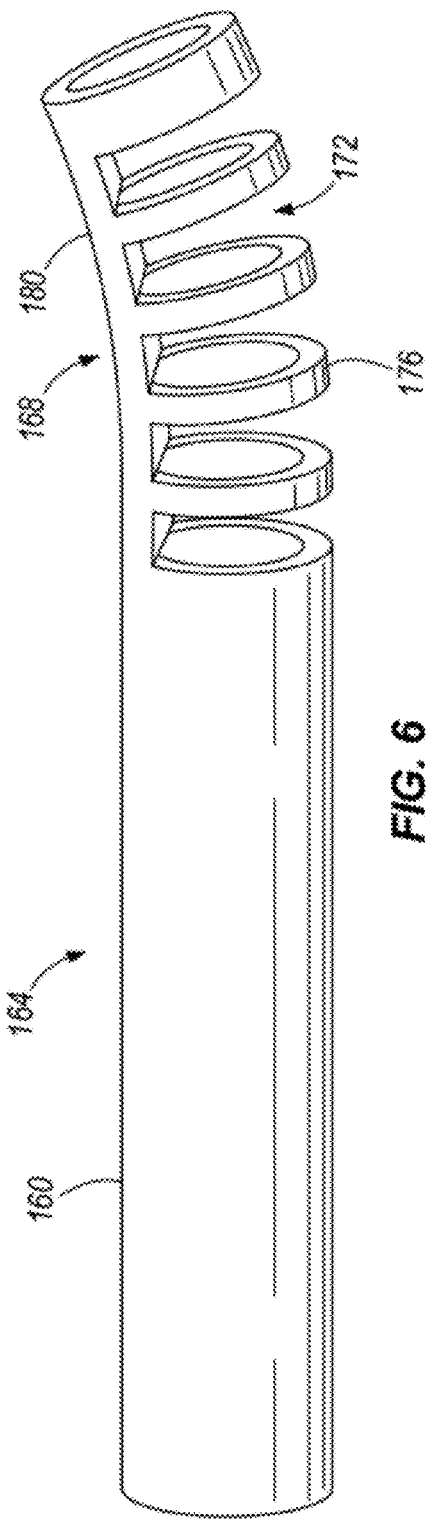

FIG. 5 illustrates a second construction of the probe 30. In this construction, the probe 30 includes a housing 130 defining a bore 134, a gradient index lens rod 138 extending from the distal end of the housing 130, and a GRIN lens 142 positioned within a distal end of the gradient index lens rod 138. The probe 30 also includes a single mode fiber 146 coupled to a piezoelectric system 150 (e.g., piezo actuator and suitable electronic circuitry to activate the piezo actuator), which is supported within the bore 134 of the housing 130. Activation of the piezoelectric system 150 is controlled by a conduit 154 extending from a proximal end of the housing 130 and to electronic circuitry. A distal end of the single mode fiber 146 is configured to move laterally within the bore 134 to scan light data at a proximal end of the gradient index lens rod 138 when the piezoelectric system 150 is activated.

FIGS. 6-9 illustrate a third construction of the probe 30. In this construction, the probe 30 includes a first tube 160 having a first portion 164 and a second portion 168. The first portion 164 is generally linear while the second portion 168 includes a plurality of notches 172 thereby defining a plurality of rings 176 interconnected by a strip 180 that is integral with the first portion 164. The second portion 168 is non-linear and forms a curvature as illustrated in FIGS. 6-9.

The first tube 160 defines a first bore 180 configured to receive a single mode fiber 184. In some constructions, the single mode fiber can have about a 125 µm diameter, or about an 80 µm diameter, or about a 50 µm diameter. Other suitable-sized diameters are also contemplated by this construction. The single mode fiber 184 can be connected or secured (e.g., with glue or other suitable fixation method) to a distal end of the second portion 168. A portion 170 of the single mode fiber 184 extends beyond the distal end of the second portion 168.

With further reference to FIG. 9, the first tube 160 is at least partially supported within a second bore 188 of a second tube 192, which is connected or secured to an inner wall of a third tube 196. The third tube 196 is connected to a housing 200 having an electromagnetic system 204 (e.g., coil, magnet, and suitable electronic circuitry to activate the coil) electrically connected to suitable electronic circuitry. The housing 200 can include a ferrule for coupling to and supporting the proximal end of the single mode fiber 184. The outer diameter of the first tube 160 is less than the inside diameter of the second tube 192 such that the first tube 160 can slide or resonate along a length of the second tube 192 when the electromagnetic system 204 is activated. The first tube 160, the second tube 192, and the third tube 196 can comprise stainless steel or other suitable materials or combinations of materials.

With continued reference to FIG. 9, the portion 170 of the single mode fiber 184 that extends from the distal end of the first tube 160 toward a distal end of the third tube 196 is positioned adjacent a GRIN imaging lens 208, which is connected to the distal end of the third tube 196. The portion 170 of the single mode fiber 184 can move laterally within the third tube 196 when the first tube 160 slides (after actuation of the electromagnetic system 204) within the second tube 192. When the first tube 160 slides within the second tube 192, the first tube 160 also slides along the single mode fiber 184 to compress the plurality of rings 176, which causes the portion 170 of the single mode fiber 184 to move laterally to scan light data near the GRIN imaging lens 208.

FIG. 10 illustrates a fourth construction of the probe 30. In this construction, the probe 30 includes a single mode fiber 220 having an actuator comprised of a memory alloy wire 224 coupled to a portion of the fiber 220. The memory alloy wire 224 can cause the single mode fiber 220 to move laterally to scan light data when a current is applied to the wire. The single mode fiber 220 can be housed within a tube as illustrated in any one of the constructions described herein, but a housing is not required.

Figure 11:
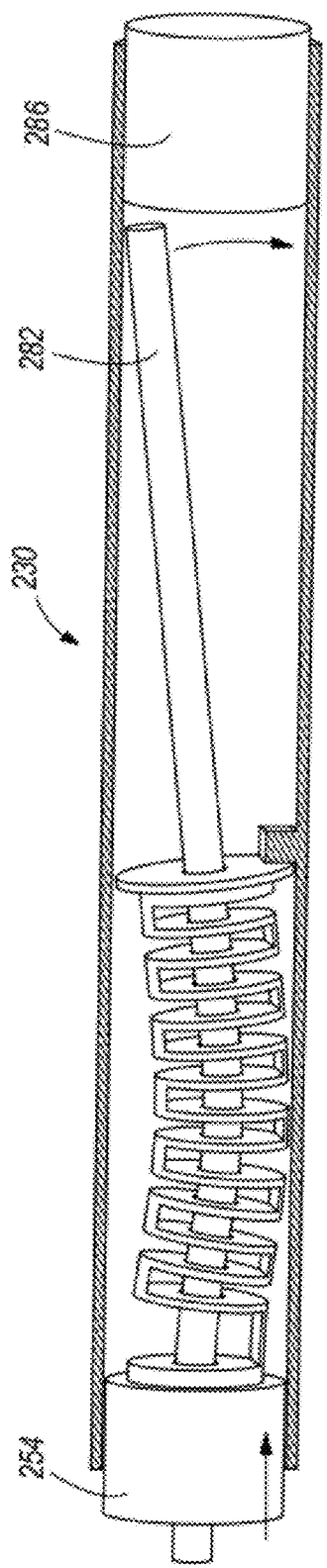
Figure 12:
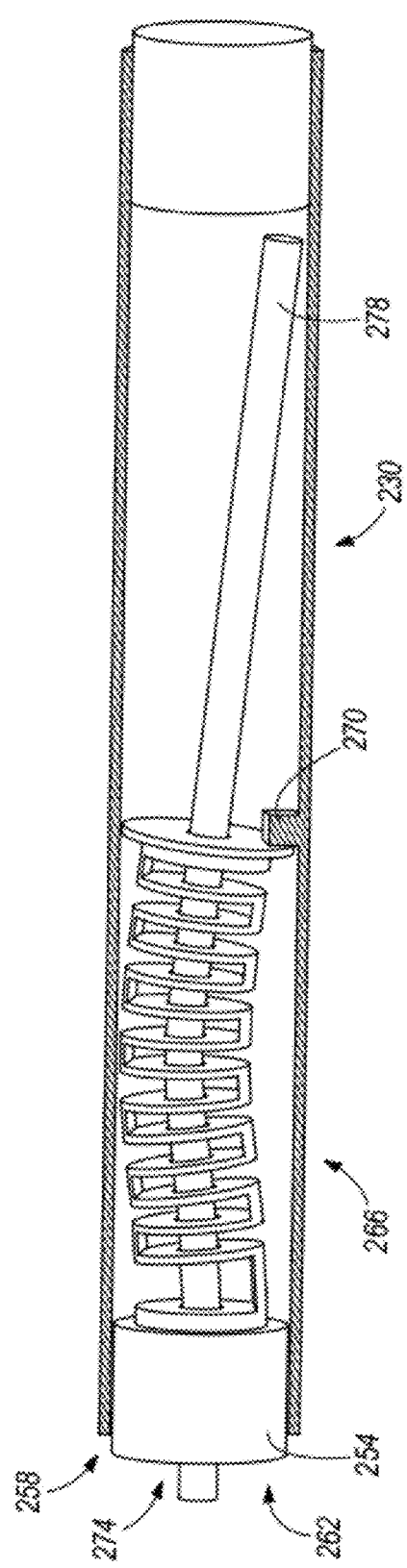

FIGS. 11-13 illustrate a fifth construction of the probe 30. In this construction, the probe 30 includes a first tube 230 connected to a housing 234 having a chamber 238. The housing 234 supports a pulsed air system having an inlet 242 coupled to an air source for periodically injecting air into the chamber 238. The housing 234 includes a diaphragm 246 biased in a first position by an elastic member 250 (e.g., a spring). The diaphragm 246 and the elastic member 250 are coupled to a second tube 254, which is positioned within a bore 258 of the first tube 230. The second tube 254 includes a first portion 262 and a second portion 266. The first portion is generally linear and is connected to the diaphragm 246 and coupled to the elastic member 250. The second portion 266 includes a spring-like structure that is non-linear and forms a curvature as illustrated in the figures. A distal end of the second portion 266 abuts with a stopper 270 on an inner wall of the first tube 230. The second tube 254 includes a bore 274 through which a single mode fiber 278 is positioned with a portion 282 of the single mode fiber 278 extending beyond a distal end of the second tube 254. A proximal end of the single mode fiber 278 also extends through the diaphragm 246 and through an aperture in the housing 234. The portion 282 of the single mode fiber 278 that extends from the distal end of the second tube 254 toward a distal end of the first tube 230 is positioned adjacent a GRIN imaging lens 286, which is connected to the distal end of the first tube 230. When the chamber 238 fills with an amount of air that overcomes the biasing force of the elastic member 250, the diaphragm 246 moves forward. When the diaphragm 246 moves forward, the second tube 254 also moves forward thereby causing the second portion 266 of the second tube 254 to flex in a sinusoidal-like pattern. This flexing of the second portion 266 causes the portion 282 of the single mode fiber 278 to move laterally to scan light data near the GRIN imaging lens 286.

FIG. 14 illustrates an alternative configuration of the fifth construction of the probe 30. In this configuration, the actuator (i.e., the inlet 242, the air source, the diaphragm 246, and the elastic member 250) can be replaced with an electromagnetic system similar to the electromagnetic systems described above. For example, an electromagnetic system or a motor can be electrically coupled to the second tube 254, such that when activated, the second tube 254 moves forward thereby causing the second portion 266 of the second tube 254 to flex in a sinusoidal-like pattern. This flexing of the second portion 266 causes the portion 282 of the single mode fiber 278 to move laterally to scan light data near the GRIN imaging lens 286.

FIG. 15 illustrates a sixth construction of the probe 30. In this construction, the probe 30 includes a single mode fiber 400 that goes through a bore within a magnet 404 that is surrounded by two coils 408. Two coils 408A and 408B, which are 180 degrees apart are situated on each side of the magnet 404. The probe 30 includes a GRIN imaging lens 412 connected to a distal end of the single mode fiber 400. In some alternative constructions, the GRIN imaging lens 412 can be connected to a distal end of a housing or tube that supports the single mode fiber 400. The coils 408A and 408B are connected to electronic circuitry such that when activated, the current through the coil 408 induces the magnet 404 to move laterally thereby causing the distal end of the single mode fiber 400 with GRIN imaging lens 412 to move laterally to scan light data at the GRIN imaging lens 412.

Figure 16:
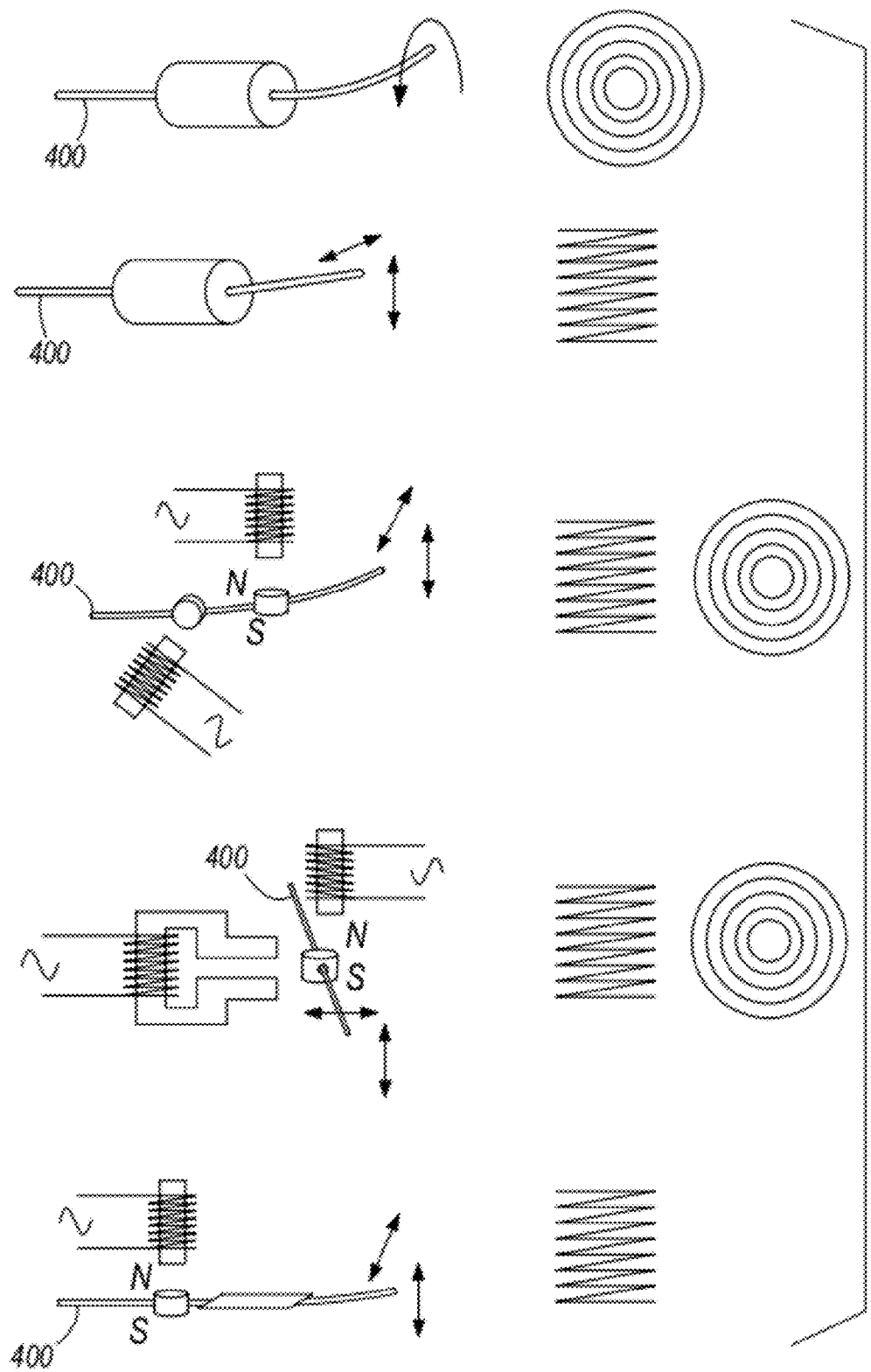

With reference to FIG. 16, other alternative constructions appropriate for the constructions illustrated in FIG. 5 or 15 can be implemented with the single mode fiber 400. For example, a piezoelectric system can be connected to the single mode fiber 400 that can be activated to rotate while adjusting the curvature of the distal portion of the single mode fiber 400. This rotation method can generate a scanning area of about 2 mm diameter. In other constructions, the piezoelectric system connected to the single mode fiber 400 can be activated to move the single mode fiber 400 forward and backward while adjusting an angle of the distal portion of the single mode fiber 400 with respect to the piezoelectric system. In this particular construction, the single mode fiber 400 can scan for light data in the X and Y directions.

With continued reference to FIG. 16, another alternative construction appropriate for the construction illustrated in FIG. 5 or 15 involves attaching two mini magnets to the single mode fiber 400 and by using electromagnetic coils to interact with the mini magnets to activate the single mode fiber 400 to move and scan for light data in the X and Y directions. In yet another alternative construction, a single mini magnet is connected to the single mode fiber 400 that interacts with signals from electromagnetic coils to activate the single mode fiber 400 to move and scan for light data in the X and Y directions. In a further alternative construction, a mini magnet and a piezo sheet is connected to the single mode fiber 400. An electromagnetic coil interacts with the mini magnet to activate the single mode fiber 400 to move and scan for light data in the X direction. In addition, the electromagnetic coil interacts with the piezo sheet to activate the single mode fiber 400 to move and scan for light data in the Y direction.

Figure 17:
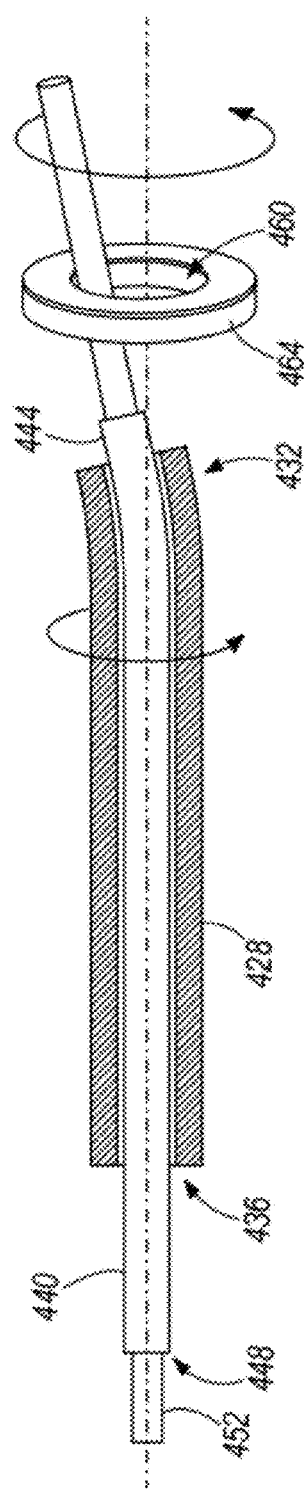
Figure 18:
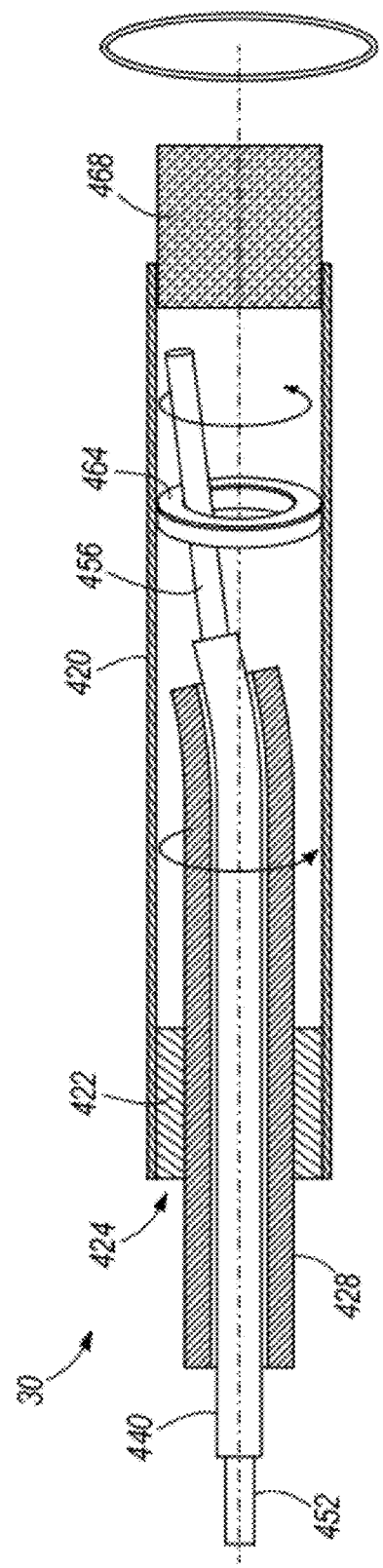

FIGS. 17-18 illustrate a seventh construction of the probe 30. In this construction, the probe 30 includes a first tube 420 that defines a first bore 424. The first tube 420 includes a bearing 422 connected to an inner wall and which is configured to support a second tube 428. The outer diameter of the second tube 428 is less than the inside diameter of the first tube 420 such that the second tube 428 can rotate within the first tube 420 when activated. The second tube 428 includes a distal portion 432 having a curvature as illustrated in the figures. The second tube 428 defines a second bore 436 configured to receive a third tube 440. The third tube 440 also includes a distal portion 444 having a curvature as illustrated in the figures. A portion of the distal portion 444 extends beyond a distal end of the second tube 428. The first tube 420, the second tube 428, and the third tube 440 can comprise stainless steel or other suitable materials or combinations of materials.

With continued reference to FIGS. 17-18, the third tube 440 defines a third bore 448 configured to receive a single mode fiber 452. A portion 456 of the single mode fiber 452 extends from the distal end of the third tube 440 toward a distal end of the first tube 420. The portion 456 is positioned through an aperture 460 of a ring 464, which is connected to the first tube 420. A distal end of the single mode fiber 452 is positioned adjacent a GRIN imaging lens 468, which is connected to the distal end of the first tube 420. The portion 456 of the single mode fiber 452 can move in a circular pattern defined by the circumference of the aperture 460 of the ring 464 within the first tube 420. This circular movement occurs when the second tube 428 is actuated (by any suitable actuator) to rotate around the third tube 440 and due to the curvature of both the second tube 428 and the third tube 440. The single mode fiber 452 scans for light data while moving in the circular pattern.

With reference to FIGS. 19-20, an alternative configuration of the seventh construction is illustrated. The difference with this alternative configuration than the configuration illustrated in FIGS. 17-18 is that the ring 464 moves forward and backward (i.e., in the Z direction). The ring 464 is connected to the bearing 422, and the bearing 422 is coupled to an actuator. When the second tube 428 is actuated to rotate, and the bearing 422 is actuated to move in the Z direction, the single mode fiber 452 scans for light data while moving in a circular pattern at different diameters. The image target is a circular band as illustrated.

Figure 21:
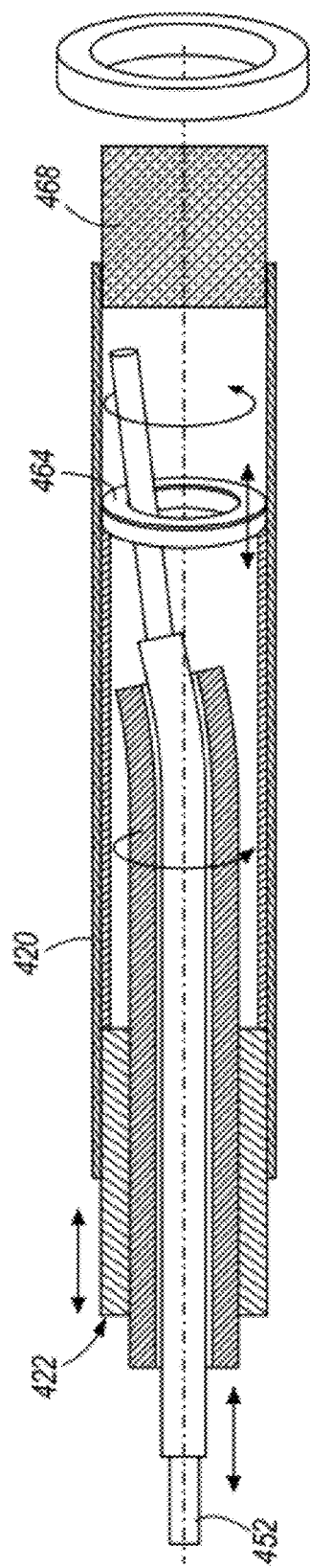

FIG. 21 illustrates another alternative configuration of the seventh construction of the probe 30. In this configuration, when the bearing 422 is actuated to move in the Z direction, the second tube 428 and the third tube 440 also move with the bearing 422. This movement causes the single mode fiber 452 to move in the Z direction which results in an image target being a circular band having a particular depth or thickness defined by how far the single mode fiber 452 moves in the Z direction.

FIGS. 22-23 illustrate an eighth construction of the probe 30. In this construction, the probe 30 includes a first tube 480 that defines a first bore 484. The first tube 480 includes a bearing 488 connected to an inner wall and which is configured to support a second tube 492. The outer diameter of the second tube 492 is less than the inside diameter of the first tube 480 such that the second tube 492 can rotate within the first tube 480 when activated. The second tube 492 includes a distal portion 496 having a curvature as illustrated in the figures. The second tube 492 defines a second bore 500 configured to receive a third tube 504. The third tube 504 also includes a distal portion 508 having a curvature as illustrated in the figures. A portion of the distal portion 508 extends beyond a distal end of the second tube 492. The first tube 480, the second tube 492, and the third tube 504 can comprise stainless steel or other suitable materials or combinations of materials.

With continued reference to FIGS. 22-23, the third tube 504 defines a third bore 512 configured to receive a single mode fiber 516. A portion 520 of the single mode fiber 516 extends from the distal end of the third tube 504 toward a distal end of the first tube 480. The portion 520 is positioned through a slit 524 of a bracket 528, which is connected to the first tube 480. A distal end of the single mode fiber 516 is positioned adjacent a GRIN imaging lens 532, which is connected to the distal end of the first tube 480. The portion 520 of the single mode fiber 516 can move in a linear pattern defined by the slit 524 of the bracket 528 within the first tube 480. This linear movement occurs when the second tube 492 is actuated (by any suitable actuator) to rotate around the third tube 504. The single mode fiber 516 scans for light data while moving in the linear pattern.

Figure 24:
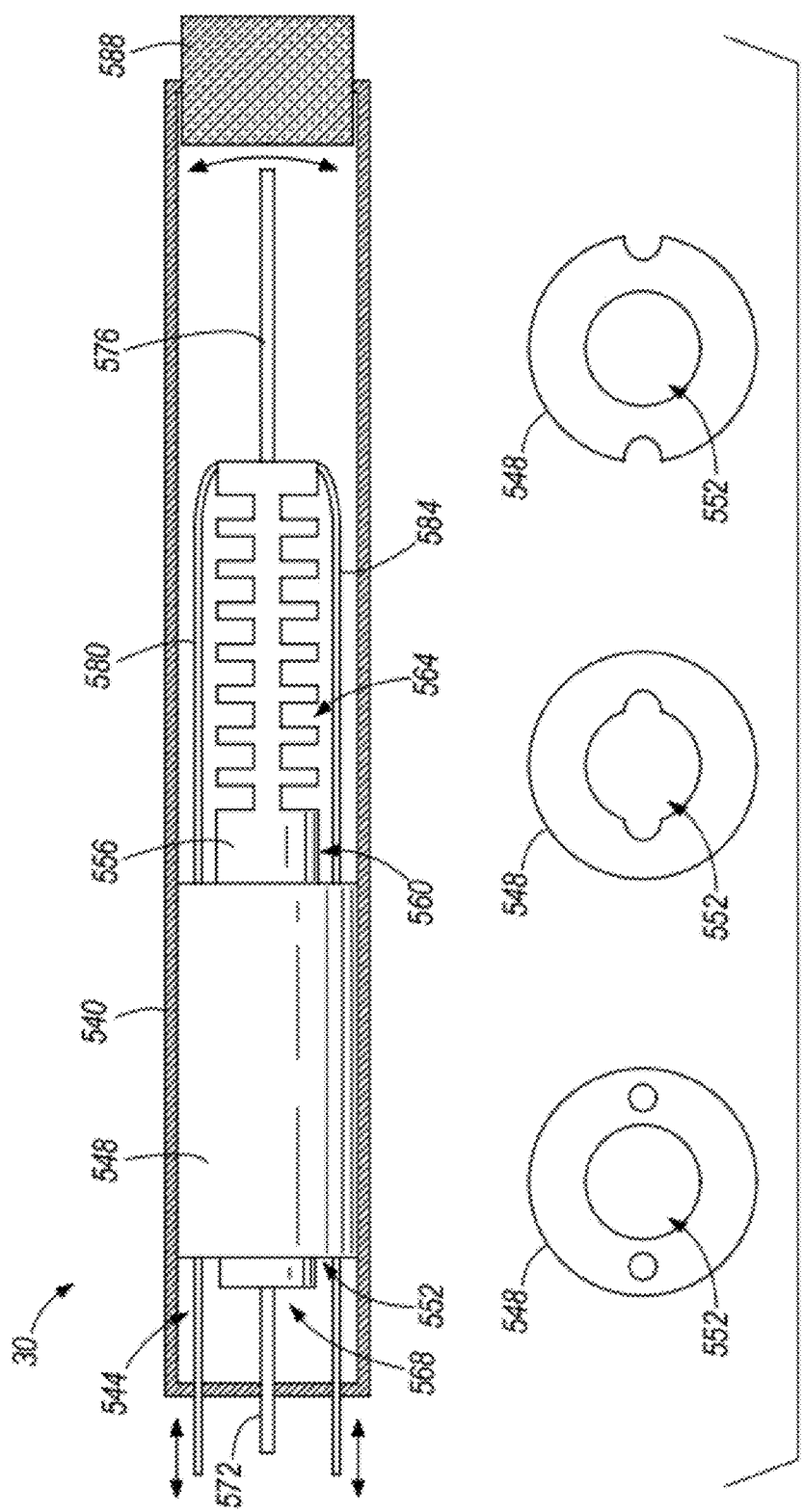
FIG. 24 is a schematic illustration of an OCT probe according to one embodiment of the present invention.
Figure 25:
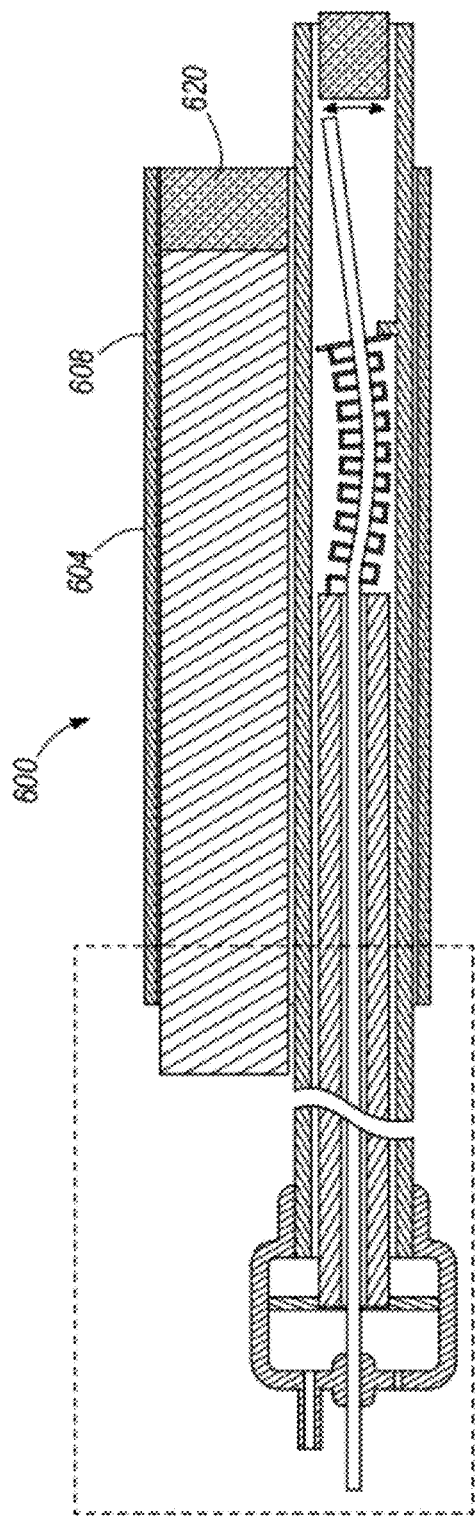
Figure 26:
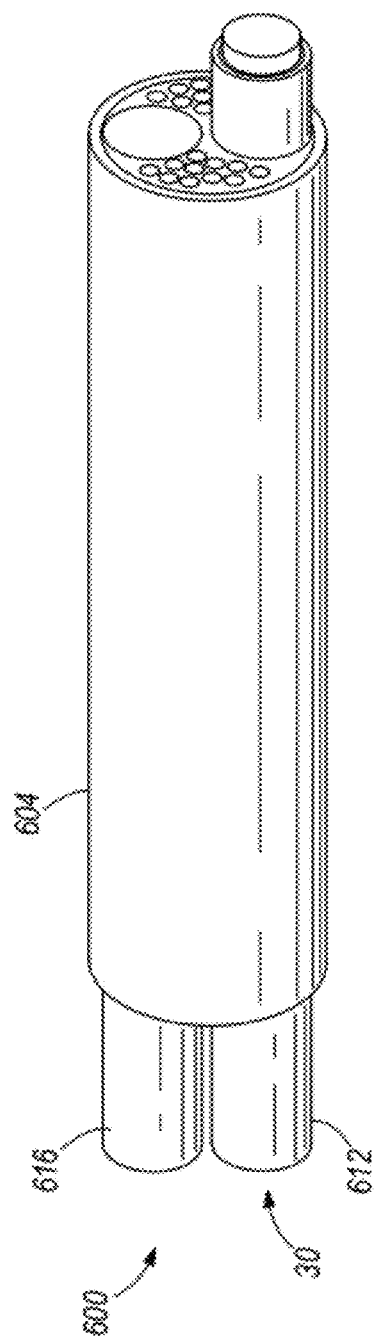
Figure 27:
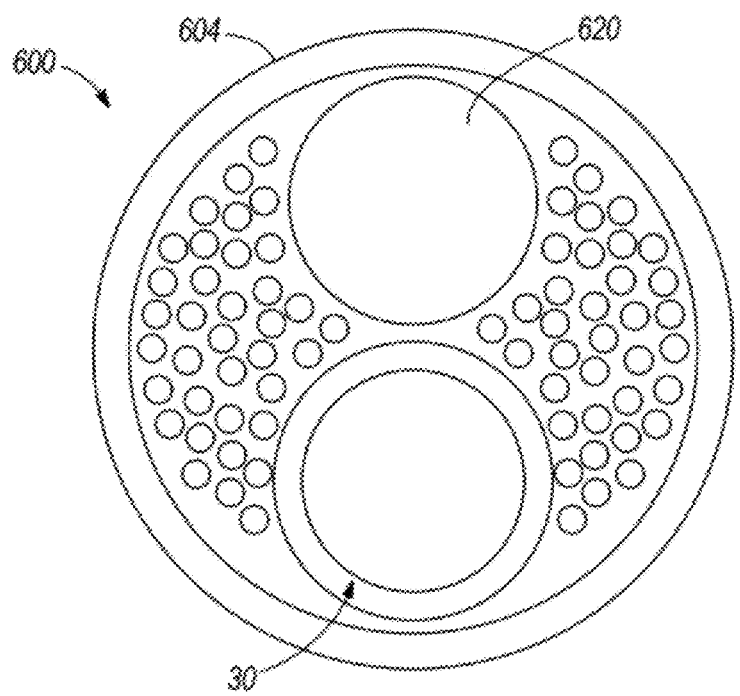
Figure 28:
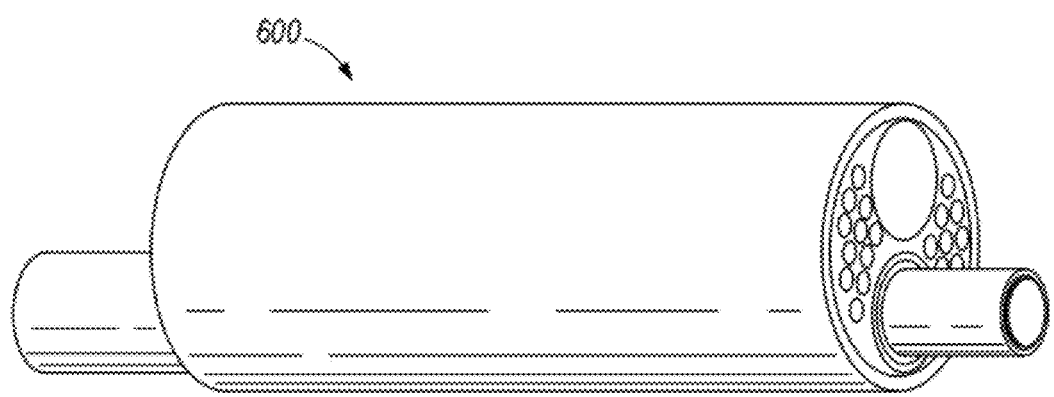

FIG. 24 illustrates a ninth construction of the probe 30. In this construction, the probe 30 includes a first tube 540 that defines a first bore 544, which is configured to support a second tube 548. The second tube 548 defines a second bore 552 configured to receive a third tube 556 and two additional bores to receive two thin wires or strings 580, 584. As illustrated in FIG. 24, the third tube 556 includes a first generally linear portion 560 and a second portion 564 having a spring-like configuration. The second portion 564 is at the distal portion of the third tube 556. The first tube 540, the second tube 548, and the third tube 556 can comprise stainless steel or other suitable materials or combinations of materials.

The third tube 556 includes a third bore 568 configured to receive a single mode fiber 572. A portion 576 of the single mode fiber 572 extends from the distal end of the third tube 556 toward a distal end of the first tube 540. The distal end of the third tube 556 is connected to two electrical conduits 580, 584, which extend through the second tube 548 and are coupled to a suitable actuator. FIG. 24 also illustrates several constructions of alternative cross-sections of the second tube 548. A distal end of the single mode fiber 572 is positioned adjacent a GRIN imaging lens 588, which is connected to the distal end of the first tube 540. The portion 576 of the single mode fiber 572 can move laterally within the first tube 540 when the actuator alternately pulls or activates the thin wires or strings 580, 584 causing the second portion 564 of the third tube 556 to bend or flex. This bending or flexing of the second portion 564 allows the distal portion 576 of the single mode fiber 572 to move laterally to scan light data at the GRIN imaging lens 588.

FIGS. 25-29 illustrate how the probe 30 is incorporated into an endoscope. An endoscope 600 includes a first tube 604. Within the first tube 604, the endoscope can include a second tube 608 and a third tube or working channel 612. The second tube 608 can support the endoscope's image fiber bundle 616 and the imaging lens 620. The third tube 612 can support the probe 30 (in any one of the constructions described above). The first tube 604 also includes numerous illumination fibers that provide a light source for illuminating the sample tissue.

The single mode fiber of each of the probes 30 described above is in communication with a processor for receiving the light data reflected from the sample. The processor is configured to generate an A-scan and/or a B-scan image from the light data. FIG. 30 illustrates a B-scan image from a probe 30 that was positioned within the eye. The white arrow identifies Schlemms canal in the eye, and the red arrow identifies the Angle.

The GRIN imaging lens of each of the probes 30 described above is polished to a particular length to define a focus point and focus length which matches the OCT imaging plane. The length of the GRIN imaging lens can be in the range of about 0.1 mm to about 3 mm. Although the GRIN imaging lens is illustrated in many of the constructions described above as being connected to the outer tube, the GRIN imaging lens can be instead connected to the distal end of the single mode fiber in those constructions. In addition, the imaging lens could be a GRIN lens, a lens ground onto a GRIN rod, an aspherical lens, a spherical lens, or a combination of these lenses.

The single mode fiber of each of the probes 30 described above can have a diameter of about 125 μm. In other constructions, the single mode fiber can have a diameter of about 50 μm or about 80 μm. In other constructions, the single mode fiber can have a customized diameter.

The probes 30 can include a single-use disposable detachable tip which includes the outer distal conduit and imaging lens. Similarly, the entire OCT probe could be a disposable single-use device.

The probe 30 can be combined with a confocal microscopy probe or an ultrasound probe for enhanced visualization of tissue samples.

The OCT probe/laser probe system 28 can be used to guide real-time surgery, such as intraocular surgeries. The probe 30 (having any one of the constructions described above) and a cutting/coagulating device, such as laser probe 40 (with treating laser system 32), can be combined in an endoscope to detect incision of a tissue layer as it occurs so that the underlying tissues are protected from injury. The probe 30 and laser probe 40 (with treating laser system 32) can be combined and used together without the endoscope. The high-resolution, forward-imaging images provided by the probe 30 can be used to evaluate sub-surface structures during surgical procedures with or without an endoscope. In addition, the probe 30 can precisely guide the depth of an endoscopic laser incision with real-time monitoring.

Figure 31:
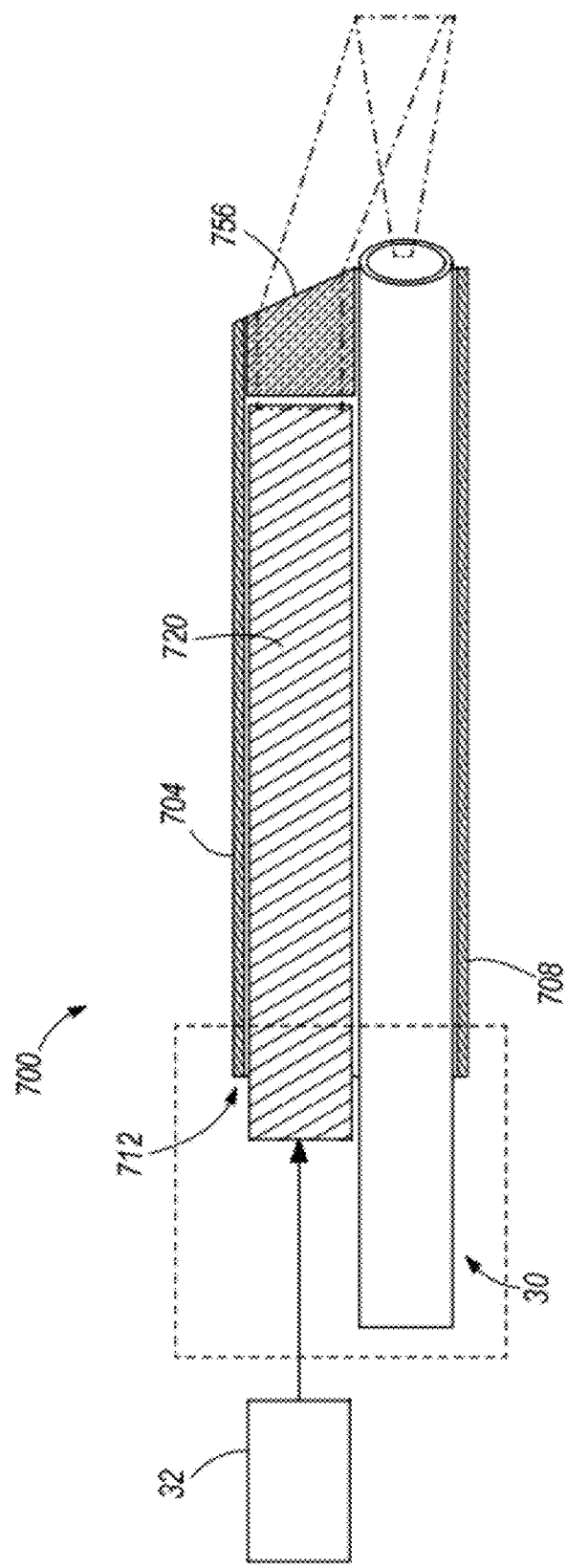

FIGS. 30-31 illustrate a device 700 configured for real-time imaging and monitoring of an electrosurgical procedure. The device 700 includes a tube 704 having a first channel 708 that supports the probe 30 and a second channel 712 that supports a cutting/coagulating tool coupled to the treating laser system 32. The cutting/coagulating tool can be hollow waveguide-based or laser fiber-based. In some constructions of the device 700, a regular laser fiber 716 is used in place of a hollow waveguide 720. The invention contemplates that other cutting/coagulating tools, such as radiofrequency based tools, can be used in combination with the probe 30 as well.

Figure 32:
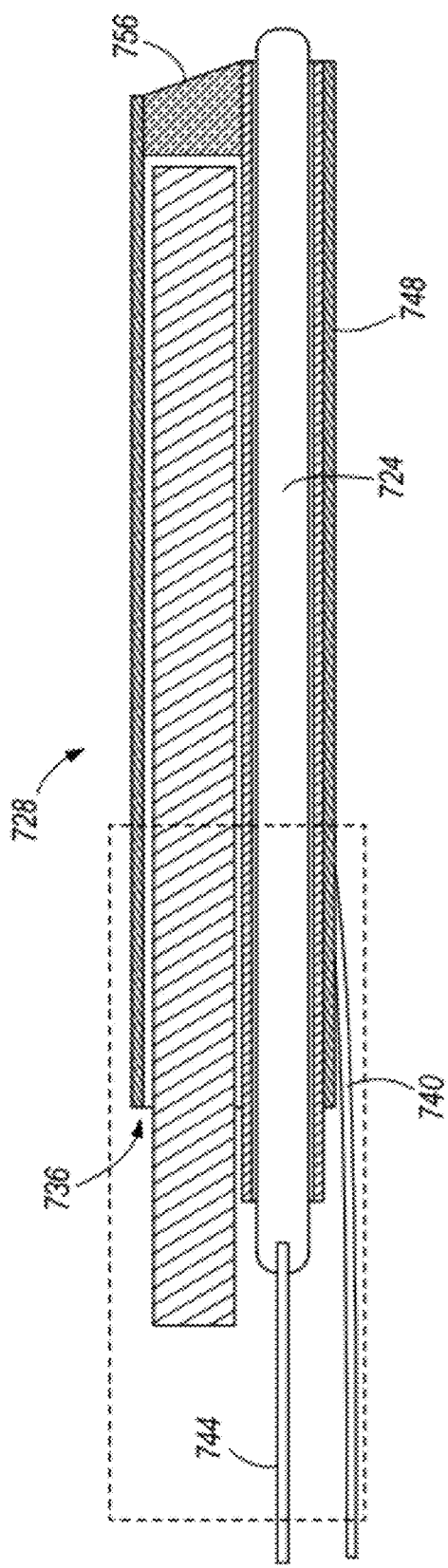
FIGS. 32-36 are schematic illustrations of a combined OCT probe and laser device according to one embodiment of the present invention positioned within the working channel of an endoscope. Some of the figures include a diathermy device.
Figure 33:
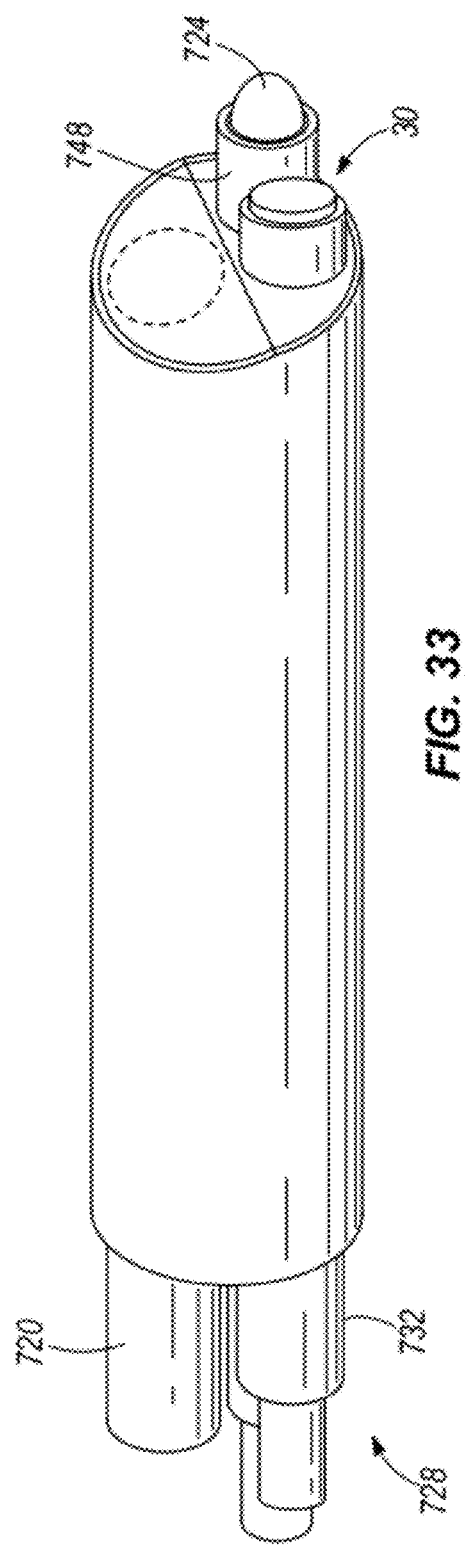
Figure 34:
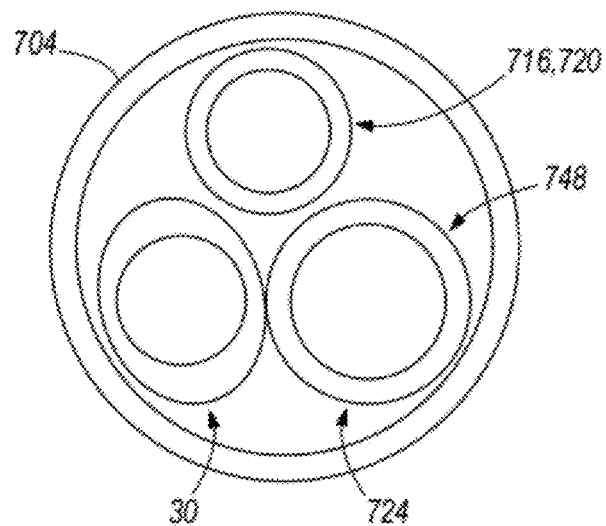

FIGS. 32-34 illustrate another construction where an optional diathermy electrosurgical tool 724 is added to device 700 to make combined device 728. The combined device 728 can be placed in the working channel of an endoscope or used alone as described above. The combined device 728 includes a first channel 732 that supports the probe 30 and a second channel 736 that supports a cutting/coagulating tool, such as a hollow waveguide 720 or a laser fiber 716, which is coupled to the treating laser system 32. In some constructions of the device 728, a regular laser fiber 716 is used in instead of the hollow waveguide 720. The invention contemplates that other cutting/coagulating tools, such as radiofrequency based tools, can be used in combination with the probe 30 as well. The combined device 728 includes a third channel 740 that supports the diathermy electrosurgical tool 724. The diathermy electrosurgical tool 724 includes a central wire 744 surrounded by Teflon insulation 748 within the third channel 740. Alternatively, the three components of combined device 728 can be connected or secured together rather than being positioned within separate channels.

Figure 35:
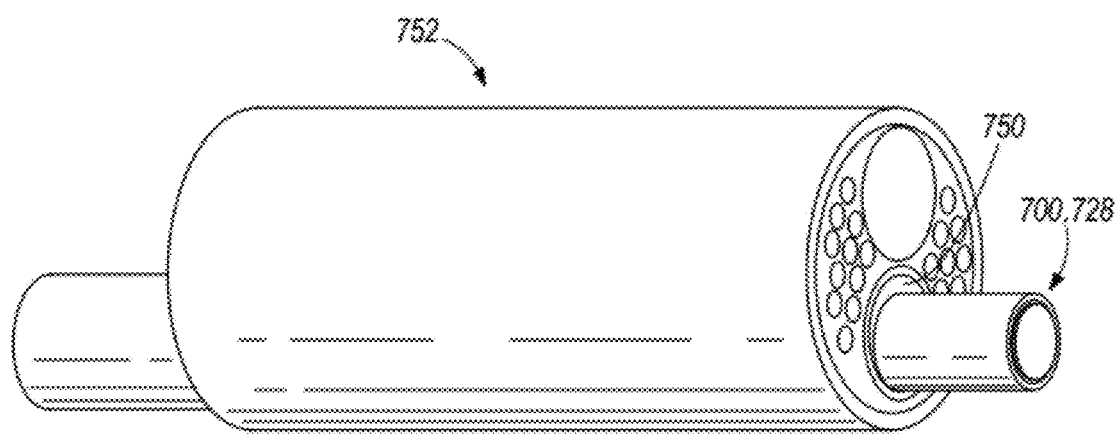
Figure 36:
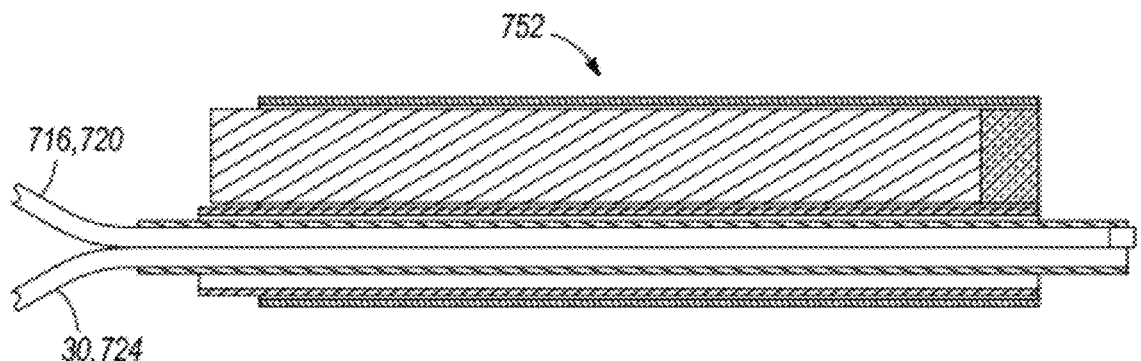

FIGS. 35-36 illustrate the device 700 or device 728 placed in the working bore 750 of a commercial endoscope 752.

As illustrated in FIG. 30, the laser fiber 716 interfaces with a prism window 754 positioned at a distal end of the laser fiber 716 to direct or focus the laser beam. As illustrated in FIG. 31, the hollow waveguide 720 also interfaces with a prism window 756 positioned at a distal end of the hollow waveguide 720. The prism windows 754, 756 are polished into a small angle at the distal side, so that the laser beam from the waveguide 720 or the laser fiber 716 will overlap with the OCT sampling beam at about 1 mm to about 15 mm (more preferably between about 3 mm to about 5 mm) from the tip of the probe 30. The prism window 756 can comprise $CaF_2$ when used with the hollow waveguide 720. An inner surface or proximal end of the prism windows 754, 756 can be polished into a focusing surface if needed.

Figure 37:
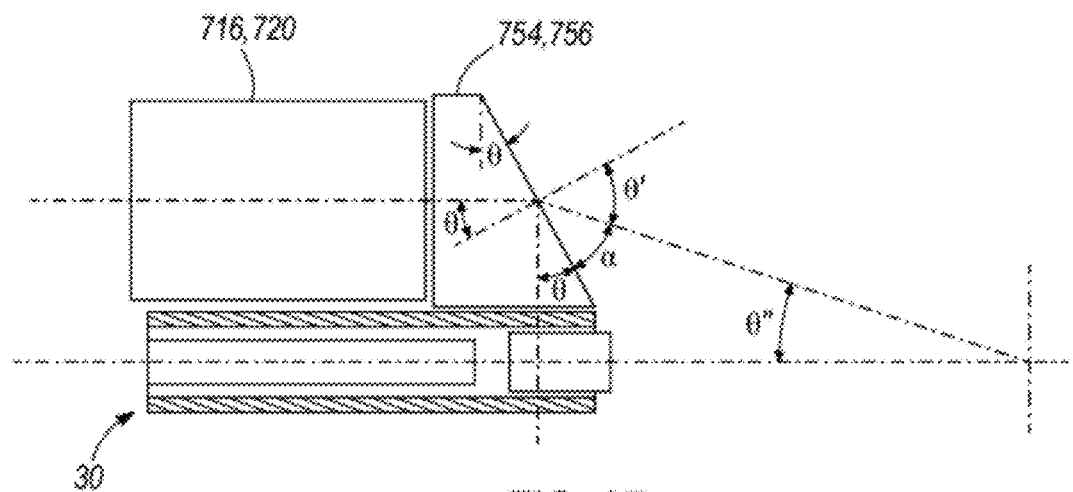
FIG. 37 is an enlarged schematic illustration of a portion of the combined OCT probe and laser device illustrated in FIGS. 30-36.
Figure 39:
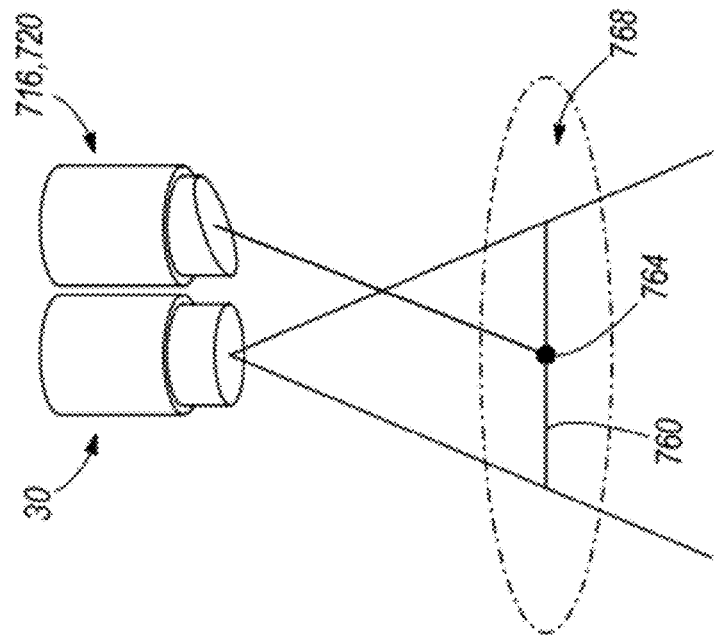
FIGS. 38-39 are schematic illustrations of a scanning and ablating process performed by the combined OCT probe and laser device illustrated in FIGS. 30-36.
Figure 38:
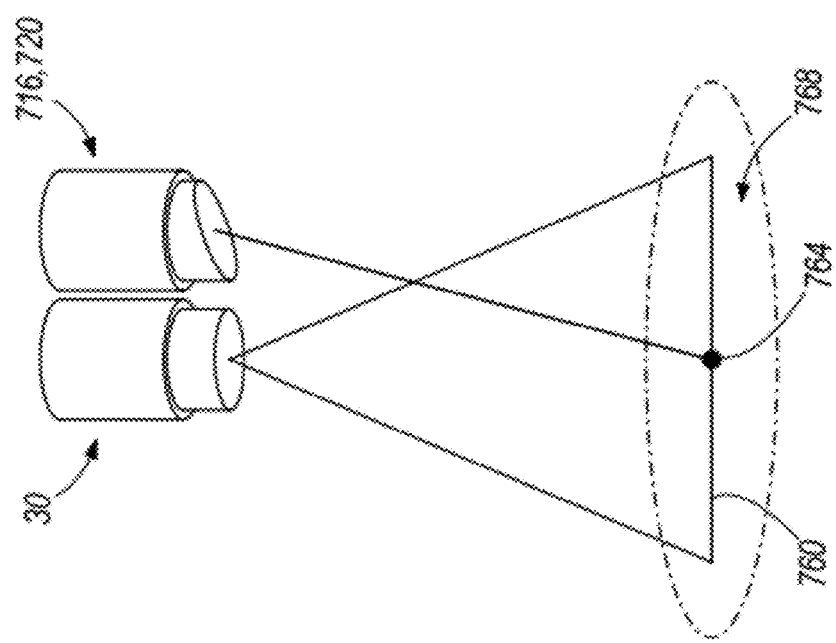

With continued reference to FIGS. 37-39, the prism windows 754, 756 are polished to a suitable angle θ such that the laser beam and the OCT scanning line are coplanar so that the target will be in focus at various distances from the tip of the probe 30. The angle θ is between about 10° to about 30° (and more preferably, 17.5°) as determined by the following:

$$\tan\theta'' = \frac{(\text{OD of hollow waveguide} + \text{OD of } OCT \text{ tube})/2}{\text{Distance from tip to target}}$$

because
θ+α+θ''=90°,
θ'+α=90°
so then θ''=θ'−θ
sin θ'=n sin θ=1.38×sin θ
(n=1.38 is the refractive index)

As illustrated in FIGS. 38-39, the OCT scanning line 760 overlaps with the laser ablation spot 764 at distances of 1 mm to 15 mm from the distal end of the device 700 from the target tissue 768.

FIGS. 32-34 illustrate an endoscope including the device 700 and a diathermy electrosurgical tool 724.

Example I

INTRODUCTION: Several groups, including ours, have identified a wavelength at 6.1 mm produced by an experimental tunable free electron laser (FEL) as capable of ablating tissue with a minimal amount of collateral damage. This is desirable for precise incisions of tissue. This laser wavelength is at a water-absorption peak and is near the 6.0 mm Amide I protein peak in the collagen spectrum. Tissues which have been treated with this wavelength include articular cartilage, fibro-cartilage, skin, cornea, and optic nerve sheath.

Previously, we developed a robust hollow-glass waveguide intraocular probe to deliver this mid-infrared energy. The waveguides also were used to transect vitreous bands that were produced by injecting fibroblasts intravitreally in an animal model. Balanced salt solution (BSS) functioned well as the transmission medium. Another surgical medium, perfluorodecalin, also permitted retinal ablation by mid-infrared laser energy. However, the FEL is a cost-prohibitive laser requiring a large amount of space and intensive upkeep. A prototype table-top laser has been developed that lases in the 6.0-7.0 mm range with potentially enough energy to incise tissue (LightAge, Inc., Somerset, N.J.). The following experiments were performed with the Light Age Q-switched Raman-shifted alexandrite laser tuned to the same wavelength of 6.1 lam delivered through a handheld prototype retinal probe. OCT is commonly used in the clinic to evaluate retinas in patients. A 25-gauge forward-imaging intraocular OCT probe was developed and attached to an 840 nm OCT engine (Bioptigen, Inc., Durham, N.C.) to attempt imaging the depth of the retinal incisions.

METHODS: A miniature 25-gauge forward-imaging probe was designed, developed and optimized to use with an 840 nm spectral domain optical coherence tomography (SDOCT) system (Bioptigen, Inc., Durham, N.C.) Its imaging parameters were determined.

Ten fresh cadaver porcine eyeballs were cut into 3-4 petals to allow the eyes to lie flat on a Petri dish, with the retina exposed. The vitreous was removed. The retinal tissue was kept moist with frequent applications of balanced saline. The Q-switched Raman-shifted alexandrite laser was tuned to 6.1 μm and the beam was directed into the glass-hollow waveguide through a $CaF_2$ focusing lens (f=100 mm). The waveguide was positioned within a customized handheld laser probe. The laser energy passed through a $CaF_2$ window on the probe tip to form a 200 μm diameter spot on the retinal petal. The average laser pulse energy was altered from 0.2-1.1 mJ/pulse at a repetition rate of 10 Hz. Holes and incisions several centimeters in length were made. The surgeon examined each test cut under an operating microscope. A photograph of an ablated retinal petal was acquired. The customized 25-gauge intraocular SDOCT probe was used to image/evaluate the incisions shown in FIG. 40.

RESULTS: An OCT probe was developed with the scanning driver within the handpiece. The SDOCT fiber-scanning probe transmits power of 500 mW. The 25-gauge forward-imaging probe is currently able to image retinal blood vessels and lased retinal incisions when held 2 to 3 mm from the retina.

We showed that the prototype table-top Q-switched Raman-shifted alexandrite laser system delivered a narrow spectral profile and a round nearly Gaussian beam profile when tuned at 6.1 μm. The 6.1 μm energy transmission was 20% through the 1.5 meter long waveguide and handpiece.

Figure 40:
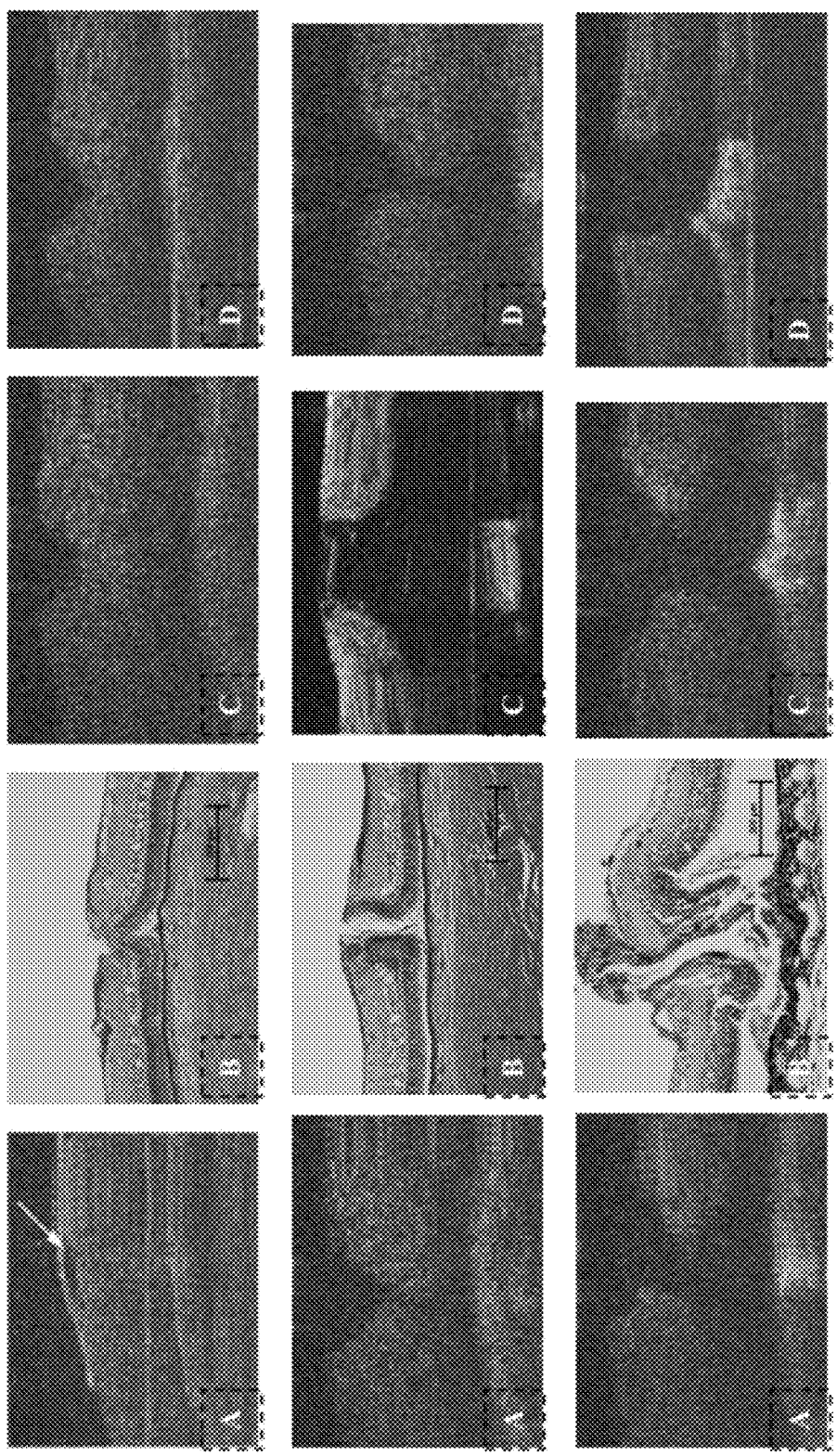
FIG. 40 is a pictorial illustration of actual retinal OCT images of a laser incision. The imaging was performed after the incision.

Our retinal experiments indicated that the laser was capable of producing retinal incisions as low as 0.4 mJ at 6.1 μm through a handheld 25-gauge retinal probe. More uniform incisions were obtained with the laser output between 0.4-0.7 mJ. This successfully incised the retina while occasionally affecting the choroid directly underneath. There was minimal damage to surrounding retinal tissue. The handheld OCT probe has an axial resolution of 6 μm and the lateral resolution approximates 40-60 μm. FIG. 40 includes histological and OCT examples of the laser's effect upon the originally attached retinas. The images demonstrate the optimal effect of a partial-thickness or full-thickness retinal incision with no disruption of the retinal pigment epithelium or choroid. On occasion, the retina was partially incised (FIG. 40, row 1, C,D). On occasion the retinal incision also involved the underlying retinal pigment epithelium with or without extension into the choroid (FIG. 40, row 3, C,D). Although, laser incision of attached retina is not a common clinical procedure, we performed ablation studies of attached retina primarily for the purpose of testing the OCT imaging capability.

CONCLUSIONS: These results demonstrate the ability of the forward-imaging 25-gauge OCT probe to display the retina incisions made with a mid-IR laser. This is a highly significant accomplishment, given that these retinas are not detached, but are in contact with the choroid. It will be much easier to avoid cutting the choroid in the case of a raised, detached retina, with absorbing fluid between the retinal and the choroidal layers. With future successful delivery of these laser pulses combined with surgical intraocular OCT probes, there is potential to greatly improve the efficacy and precision of retinal lasing. A miniature intraoperative probe was developed that is capable of forward-imaging with OCT within the eye. It has the future potential to guide real-time intraocular surgery.

Example II

Figure 41:
FIG. 41 is a pictorial illustration of actual retinal OCT images of a laser incision taken while lasing.

FIG. 41 illustrates real-time imaging which occurred with 6.1 μm laser ablation of retina with one construction of the device 700 as shown in the sequential images from a video.

Various features and advantages of the invention are set forth in the following claims.

What is claimed is:

1. An imaging and electrical surgical device comprising:
    a housing including a distal end and a proximal end;
    an actuator coupled to the housing and positioned at the proximal end of the housing;
    a single mode fiber positioned within the housing, the single mode fiber being configured to move laterally when activated by the actuator;
    a lens connected to the housing and positioned at the distal end of the housing, the lens having a diameter substantially similar to a diameter of the housing and configured to remain stationary when the single mode fiber moves within the housing, the single mode fiber configured to scan light data transmitted through the lens and reflected from a sample positioned in front of a distal end of the housing;
    an electrical surgical tool positioned adjacent to the single mode fiber; and
    a prism window positioned at a distal end of the electrical surgical tool, the prism window including a front surface defining an angle with respect to a centerline of the housing, the prism window configured to bend a light signal generated by the electrical surgical tool.

2. The imaging and electrical surgical device of claim 1 wherein the electrical surgical tool is a laser.

3. The imaging and electrical surgical device of claim 2 wherein laser delivery includes a hollow waveguide.

4. The imaging and electrical surgical device of claim 2 wherein laser delivery includes a multimode laser fiber.

5. The imaging and electrical surgical device of claim 1 wherein the electrical surgical tool is a radio-frequency device.

6. The imaging and electrical surgical device of claim 5 wherein the electrical surgical tool delivery includes a wire.

7. The imaging and electrical surgical device of claim 1 wherein the angle is between about 10 degrees and 30 degrees.

8. The imaging and electrical surgical device of claim 1 wherein the actuator includes one of an electromagnetic system, a piezoelectric system, and a pulsed air system.

9. The imaging and electrical surgical device of claim 1 wherein a beam, output from the electrical surgical tool, exiting the prism window is coplanar with the scan of the sample performed by an OCT single mode fiber.

10. The imaging and electrical surgical device of claim 9 wherein the beam and scan at least partially overlap at about 1 mm to 15 mm from a distal end of the device.

11. The imaging and electrical surgical device of claim 1 wherein the lens is a GRIN imaging lens.

12. The imaging and electrical surgical device of claim 11 wherein the GRIN imaging lens is polished to a particular length to define a focus point and a focus length which matches an OCT imaging plane.

13. The imaging and electrical surgical device of claim 1 wherein the lens is one of a lens ground onto a GRIN rod, an aspherical lens, a spherical lens, and a combination thereof.

14. The imaging and electrical surgical device of claim 1 wherein the single mode fiber has about a 125 μm diameter.

15. The imaging and electrical surgical device of claim 1 wherein the single mode fiber has about a 50 μm diameter.

16. The imaging and electrical surgical device of claim 1 wherein the single mode fiber has about an 80 μm diameter.

17. The imaging and electrical surgical device of claim 1 wherein the single mode fiber is in communication with a processor for receiving the light data, the processor configured to generate a B-scan image from the light data.

18. The imaging and electrical surgical device of claim 1 wherein the single mode fiber is in communication with a processor for receiving the light data, the processor configured to generate an A-scan image from the light data.

19. A method of monitoring a surgical procedure of a patient, the method comprising:
    inserting an endoscope through a lumen in the patient to a target, the endoscope including
        an electrical surgical tool including a prism window positioned at a distal end of the electrical surgical tool and including a front surface defining an angle with respect to a centerline of the endoscope, and
        an imaging device comprising
            a housing having a distal end and a proximal end;
            an actuator coupled to the housing and positioned at the proximal end of the housing;
            a single mode fiber positioned within the housing, the single mode fiber being configured to move laterally when activated by the actuator, and
            a lens connected to the housing and positioned at the distal end of the housing, the lens having a diameter substantially similar to a diameter of the housing and configured to remain stationary when the single mode fiber moves within the housing, the single mode fiber configured to scan for light data transmitted through the lens and reflected from the target;
    activating the electrical surgical tool to incise the target in the patient;
    activating the single mode fiber to laterally scan for light data;
    collecting the light data reflected from the target;
    generating one of an A-scan image and a B-scan image of the collected light data in real-time as the electrical surgical tool incises the target; and
    monitoring the incision based on the generated A-scan image or B-scan image.

20. The method of claim 19 wherein the B-scan image is an image of the target at least 1 mm to 15 mm forward of a distal end of the endoscope.

21. The method of claim 19 wherein the electrical surgical tool is a laser.

22. The method of claim 19 further comprising a processor coupled to the single mode fiber and configured to receive the light data and to generate the A-scan image or the B-scan image.

23. The method of claim 22 wherein the electrical surgical tool is coupled to the processor, and further comprising deactivating the electrical surgical tool when one of the A-scan image and the B-scan image identifies that the incision is within a predefined tolerance.

24. A method of monitoring a surgical procedure of a patient, the method comprising:
    inserting an electrical surgical tool and an imaging device through a lumen in the patient to a target, the electrical surgical tool including a prism window positioned at a distal end of the electrical surgical tool and including a front surface defining an angle configured to bend a light signal generated by the electrical surgical tool on a target in the patient, the imaging device including
        a housing having a distal end and a proximal end, a single mode fiber positioned within the housing, and a lens connected to the housing and positioned at the distal end of the housing, the lens having a diameter substantially similar to a diameter of the housing and configured to remain stationary when the single mode fiber moves within the housing, the lens configured to receive light transmitted therethrough and reflected from the target;

activating the electrical surgical tool to incise the target in the patient;

activating the imaging device to laterally scan for light data;

collecting the light data reflected from the target;

generating one of an A-scan image and a B-scan image of the collected light data in real-time as the electrical surgical tool incises the target; and monitoring the incision based on the generated A-scan image or B-scan image.

25. The method of claim 24 wherein the B-scan image is an image of the target at least 1 mm to 15 mm forward of a distal end of the imaging device.

26. The method of claim 24 wherein the electrical surgical tool is a laser.

27. The method of claim 24 further comprising a processor coupled to the imaging device and configured to receive the light data and to generate the A-scan image or the B-scan image.

28. The method of claim 27 wherein the electrical surgical tool is coupled to the processor, and further comprising deactivating the electrical surgical tool when one of the A-scan image and the B-scan image identifies that the incision is within a predefined tolerance.

* * * * *